(12) United States Patent
Douglas et al.

(10) Patent No.: US 10,501,744 B2
(45) Date of Patent: Dec. 10, 2019

(54) PRESENTATION OF BIOACTIVE PROTEINS

(71) Applicant: INDIANA UNIVERSITY RESEARCH AND TECHNOLOGY CORPORATION, Indianapolis, IN (US)

(72) Inventors: Trevor Douglas, Bloomington, IN (US); Benjamin Harold Schwarz, Eureka, MT (US); Ranjit Koliyatt, Mount Prospect, IL (US); Masaki Uchida, Bloomington, IN (US); John Alexander Avera, Spencer, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 15/587,098

(22) Filed: May 4, 2017

(65) Prior Publication Data

US 2017/0321220 A1   Nov. 9, 2017

Related U.S. Application Data

(60) Provisional application No. 62/331,869, filed on May 4, 2016.

(51) Int. Cl.

| | |
|---|---|
| *C12P 21/06* | (2006.01) |
| *C12N 15/00* | (2006.01) |
| *C12P 21/08* | (2006.01) |
| *C07K 1/00* | (2006.01) |
| *C12N 15/62* | (2006.01) |
| *C07K 14/435* | (2006.01) |
| *C12N 15/10* | (2006.01) |
| *C12N 15/63* | (2006.01) |
| *C12Q 1/68* | (2018.01) |
| *C07K 14/705* | (2006.01) |
| *C07K 19/00* | (2006.01) |

(52) U.S. Cl.
CPC ............ *C12N 15/62* (2013.01); *C07K 14/435* (2013.01); *C07K 14/70578* (2013.01); *C12N 15/1062* (2013.01); *C12N 15/1075* (2013.01); *C12N 15/63* (2013.01); *C12Q 1/68* (2013.01); *C07K 19/00* (2013.01); *C07K 2319/00* (2013.01); *C12N 15/00* (2013.01)

(58) Field of Classification Search
None
See application file for complete search history.

(56) References Cited

U.S. PATENT DOCUMENTS

| 4,863,457 A | 9/1989 | Lee |
| 5,378,475 A | 1/1995 | Smith et al. |
| 5,443,505 A | 8/1995 | Wong et al. |
| 7,317,091 B2* | 1/2008 | Lazar ................. C07K 16/00 530/387.1 |
| 2015/0337014 A1* | 11/2015 | Catalano ............. C12N 7/00 514/20.9 |

FOREIGN PATENT DOCUMENTS

| EP | 1 450 847 A2 | 9/2004 |
| WO | WO 2003/042344 A2 | 5/2003 |
| WO | WO 2010/010051 A1 | 1/2010 |
| WO | WO 2015/164588 A1 | 10/2015 |

OTHER PUBLICATIONS

Hehlgans et al. 2005. Immunology 115:1-20 (Year: 2005).*
Marcos et al. 2015. J. Biol Chem. 290:6697-6704 (Year: 2015).*
Zhou et al. 2014. Circ.Res. 114:706-716 (Year: 2014).*
North. 2016. Phil. Trans R Soc B 371:20150427 (Year: 2016).*
Shi et al. 2015. Int. J. Mol. Sci. 16:18836-18864 (Year: 2015).*
Liu et al. 2014. Best Pract.Res. Clin. Endocrinol. Metab. 28: 25-31 (Year: 2014).*
Aggarwal et al. 2012. Blood. 119:651-665 (Year: 2012).*
Lander et al., "Bacteriophage Lamda Stabilization by Auxiliary Protein gpD; Timing, Location, and Mechanism of Attachment Determined by Cryo-EM," *Structure* 16: 1399-1406 (2008).
Qin et al., "Structure of the Small Outer Capsid Protein, Soc: a Clamp for Stabilizing Capsids of T4-like Phages," *J Mol Biol* 395(4): 728-741 (2010).
Remington, *The Science and Practice of Pharmacy*, 21st Edition, Lippincott Williams & Wilkins, Philadelphia, PA (2001)—Table of Contents (4 pgs.).
Schwarz et al., "Symmetry Controlled, Genetic Presentation of Bioactive Proteins on the P22 Virus-like Particle Using an External Decoration Protein," *ACS Nano* 9(9): 9134-9147 (2015).
Tang et al., "Highly Discriminatory Binding of Capsid-Cementing Proteins in Bacteriophage L," *Structure* 14: 837-845 (2006).
Xiang et al., "Structure of bacteriophage ø29 head fibers has a supercoiled triple repeating helix-turn-helix motif," *PNAS* 108(12): 4806-4810 (2011).
*Harrison's Principles of Internal Medicine*, 17th Edition, Eugene Braunwald et al., Editors, Section 6: *Hematology and Oncology*, pp. 321-410 (2009).

* cited by examiner

*Primary Examiner* — Shulamith H Shafer
(74) *Attorney, Agent, or Firm* — Woodard, Emhardt, Henry, Reeves & Wagner, LLP

(57) ABSTRACT

The invention provides a fusion protein comprising an antigen binding domain linked to a bacteriophage decoration (Dec) protein along with a polynucleotide comprising the nucleic acid sequence of the fusion protein and a vector comprising the polynucleotide. Additionally, the invention provides a composition comprising the fusion protein and a virus-like particle (VLP), and a method of treating a disease in a mammal comprising administering a therapeutically effective amount of the composition to the mammal. The invention also provides a method of vaccinating against a disease comprising administering a composition comprising the fusion protein and a VLP encapsulating a protein.

21 Claims, 22 Drawing Sheets
(11 of 22 Drawing Sheet(s) Filed in Color)
Specification includes a Sequence Listing.

| construct | MW (MDa) | Dec monomers | Rh (nm) | retention shift (min) |
|---|---|---|---|---|
| EX | 20.5±0.2 | 0±12 | 28.4±0.7 | 0±0.008 |
| EX+DecWT | 23.0±0.1 | 155±6 | 29.6±0.7 | 0.619±0.005 |
| DecΔ11 | 23.6±0.2 | 214±14 | 30.1±0.7 | 0.595±0.005 |
| DecΔ20 | 20.5±0.2 | 0±15 | 28.6±0.6 | 0.076±0.009 |
| EX+DecCD40L[b] | 22.4±0.2 | 51±5 | 30.2±0.7 | 0.729±0.008 |
| EX+DecSelf | 22.6±0.2 | 114±11 | 29.6±0.8 | 0.500±0.005 |
| PC | 22.8±0.7 | 0±43 | 26.4±0.5 | 0±0.001 |
| PC+DecWT | 23.2±0.2 | 24±14 | 26.6±0.7 | 0.03±0.008 |

[a] The number of Dec monomers was calculated via the difference between bound and control particle molecular weight. All uncertainty reflects one standard deviation. For EX and PC controls "Dec monomer" standard deviation reflects the number of DecWT monomers. [b] The DecCD40L sample was incubated with less than a full equivalent of the DecCD40L construct per anticipated Dec site due to interactions of DecCD40L with the column. This also introduces significant uncertainty into the retention shift for this construct.

FIGURE 3G

| construct | $K_{a1}$ (M⁻¹ s⁻¹) | $K_{d1}$ (s⁻¹ × 10⁻⁴) | $K_{D1}$ (nM) | $K_{a2}$ (M⁻¹ s⁻¹) | $K_{a2}$ (s⁻¹ × 10⁻⁴) | $K_{D2}$ (nM) |
|---|---|---|---|---|---|---|
| DecWT | 11540±30 | 1.06±0.06 | 9.2±0.5 | 1980±146 | 29.8±0.6 | 1502±115 |
| DecWT[b] | 12561±20 | 0.032 | 0.255±0.004 | 4066±32 | 18.2±0.2 | 445.9±5 |
| DecΔ11 | 9203±18 | 0.44±0.06 | 4.8±0.6 | 38311±349 | 44±2 | 155±8.7 |
| DecΔ20 | 70.6±0.3 | 2.4±0.1 | 3450±30 | – | – | – |
| DecCD40L | 6439±4 | 2.0±0.03 | 30.8±0.4 | 4824±93 | 68±1 | 1421±38 |
| DecSelf | 11246±80 | 2.0±0.03 | 18.3±0.3 | 2193±109 | 32.3±0.3 | 145.9±7.3 |

[a]All parameters are the result of global fitting across three full concentration set replicates (1-1580 nM Dec). Error reflects one standard deviation as reported by the global fit utility in IGOR PRO. DecΔ20 parameters are the result of a single-site fit and concentrations sets spanning 31.6-31,600 nM. [b]The second set of DecWT parameters is the result of fitting with $K_{D1}$ fixed at 3.2 × 10⁻⁶ s⁻¹ reflecting 4 h dissociation runs.

FIGURE 6E

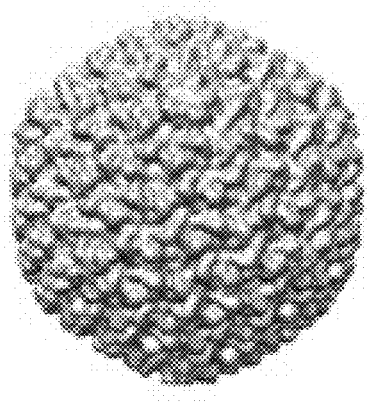
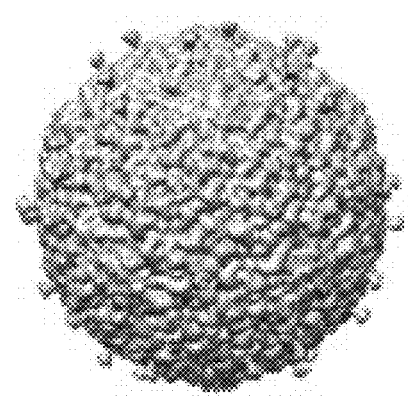
FIGURE 11A          FIGURE 11B
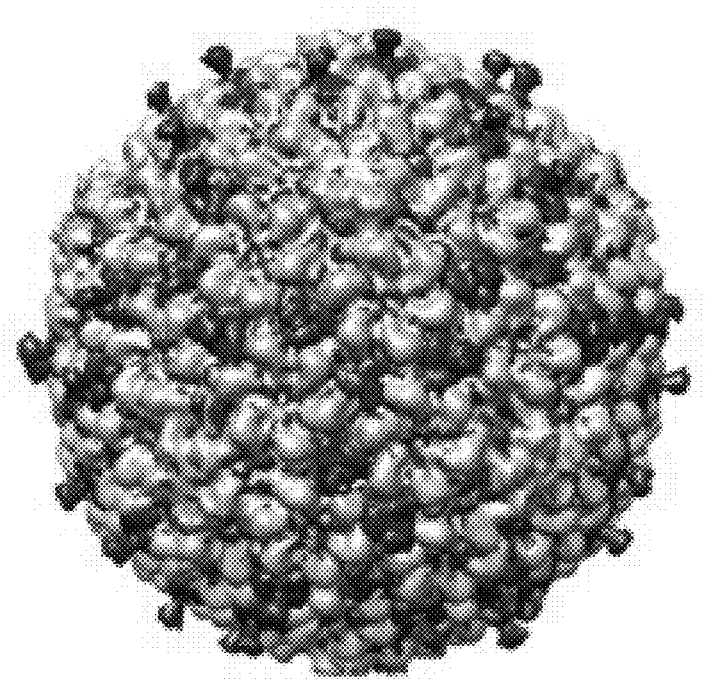
FIGURE 11C

SEQUENCE LISTING

<160> NUMBER OF SEQ ID NOS: 32

<210> SEQ ID NO 1
<211> LENGTH: 8
<212> TYPE: DNA
<213> ORGANISM: Artificial Sequence
<220> FEATURE:
<223> OTHER INFORMATION: Synthetic sequence

<400> SEQUENCE: 1 sgsgssgs                                                              8

<210> SEQ ID NO 2
<211> LENGTH: 307
<212> TYPE: PRT
<213> ORGANISM: Artificial Sequence
<220> FEATURE:
<223> OTHER INFORMATION: Synthetic Sequence

<400> SEQUENCE: 2

Met Gly Ser Ser His His His His His Ser Leu Val Pro Arg Gly
1               5                   10                  15

Ser Gln Asp Pro Met Ala Asn Pro Asn Phe Thr Pro Ser Trp Pro Leu
            20                  25                  30

Tyr Lys Asp Ala Asp Gly Val Tyr Val Ser Ala Leu Pro Ile Lys Ala
        35                  40                  45

Ile Lys Tyr Ala Asn Asp Gly Ser Ala Asn Ala Glu Phe Asp Gly Pro
    50                  55                  60

Tyr Ala Asp Gln Tyr Met Ser Ala Gln Thr Val Ala Val Phe Lys Pro
65                  70                  75                  80

Glu Val Gly Gly Tyr Leu Phe Arg Ser Gln Tyr Gly Glu Leu Leu Tyr
                85                  90                  95

Met Ser Lys Thr Ala Phe Glu Ala Asn Tyr Thr Ser Ala Ser Gly Ser
            100                 105                 110

Val Ala Asn Ala Glu Thr Ala Asp Lys Leu Ser Thr Ala Arg Thr Ile
        115                 120                 125

Thr Leu Thr Gly Ala Val Thr Gly Ser Ala Ser Phe Asp Gly Ser Ala
    130                 135                 140

Asn Val Thr Ile Glu Thr Thr Ser Gly Ser Gly Ser Gly Ser Gln
145                 150                 155                 160

Lys Gly Asp Gln Asn Pro Gln Ile Ala Ala His Val Ile Ser Glu Ala
                165                 170                 175

Ser Ser Lys Thr Thr Ser Val Leu Gln Trp Ala Glu Lys Gly Tyr Tyr
            180                 185                 190

Thr Met Ser Asn Asn Leu Val Thr Leu Glu Asn Gly Lys Gln Leu Thr
        195                 200                 205

Val Lys Arg Gln Gly Leu Tyr Tyr Ile Tyr Ala Gln Val Thr Phe Cys
210                 215                 220

Ser Asn Arg Glu Ala Ser Ser Gln Ala Pro Phe Ile Ala Ser Leu Cys
225                 230                 235                 240

Leu Lys Ser Pro Gly Arg Phe Glu Arg Ile Leu Leu Arg Ala Ala Asn
                245                 250                 255

Thr His Ser Ser Ala Lys Pro Cys Gly Gln Gln Ser Ile His Leu Gly
            260                 265                 270

Gly Val Phe Glu Leu Gln Pro Gly Ala Ser Val Phe Val Asn Val Thr
        275                 280                 285

Asp Pro Ser Gln Val Ser His Gly Thr Gly Phe Thr Ser Phe Gly Leu
    290                 295                 300

Leu Lys Leu
305

<210> SEQ ID NO 3
<211> LENGTH: 932
<212> TYPE: DNA
<213> ORGANISM: Artificial Sequence
<220> FEATURE:
<223> OTHER INFORMATION: Synthetic sequence

<400> SEQUENCE: 3
ccatgggcag cagccatcac caccatcacc acagcctcgt cccgcgcggc tcacaggatc      60
ccatggcaaa cccaaacttc acgccatcat ggcctctata caaagatgct gacggtgtat     120

```
atgtgtctgc gcttccgatt aaagctatca aatacgctaa tgacggaagt gcaaacgcag    180
aattcgacgg cccgtatgct gaccagtaca tgtcagcgca aacagtagcc gtattcaagc    240
cggaggttgg cggatatctg ttccggagcc agtacggcga gctgctctat atgagcaaga    300
cagcatttga agctaactac acttctgcaa gcggttcagt agctaatgca gagacggcgg    360
ataagttatc tactgcccgc actatcacac taaccggagc ggtcacaggt tcagcgtcct    420
ttgatggttc ggctaacgtg actatcgaaa caacatcagg aagtggatcc tccggctctc    480
agaaaggtga ccagaatccg caaattgcag cgcatgttat cagcgaagct tcctctaaga    540
ctacctctgt tctgcagtgg gctgagaagg gttattatac gatgagcaac aatctggtga    600
ccctggaaaa cggtaaacaa ctgacggtta acgtcaggg tctgtactat atctacgcgc    660
aggtgacctt ctgttccaac cgtgaagctt cctcccaggc accatttatt gcgagcctgt    720
gtctgaaatc tccgggccgt tcgaacgta tcctgctgcg cgcggcgaac acccactcca    780
gcgcgaaacc gtgcggccaa cagagcatcc acctgggtgg cgtattcgaa ctgcaaccgg    840
gtgcgtctgt cttcgtgaac gtcactgatc cgtcccaggt gtcccacggc accggtttca    900
cttccttcgg tctgctgaag ctgtaagagc tc                                  932
```

<210> SEQ ID NO 4
<211> LENGTH: 65
<212> TYPE: DNA
<213> ORGANISM: Artificial Sequence
<220> FEATURE:
<223> OTHER INFORMATION: Synthetic sequence

<400> SEQUENCE: 4

```
cggcaactat acctgcgaag tgaccgaact gacccgcgaa ggcgaaacca ttattgaact    60
gaaaa                                                                65
```

<210> SEQ ID NO 5
<211> LENGTH: 73
<212> TYPE: DNA
<213> ORGANISM: Artificial Sequence
<220> FEATURE:
<223> OTHER INFORMATION: Synthetic sequence

<400> SEQUENCE: 5

```
agcttttca gttcaataat ggtttcgcct tcgcgggtca gttcggtcac ttcgcaggta    60
tagttgccga gct                                                       73
```

<210> SEQ ID NO 6
<211> LENGTH: 40
<212> TYPE: DNA
<213> ORGANISM: Artificial Sequence
<220> FEATURE:
<223> OTHER INFORMATION: Synthetic sequence

<400> SEQUENCE: 6

```
cgaaaccatt attgaactga ataaaagct tgcggccgca                            40
```

<210> SEQ ID NO 7
<211> LENGTH: 40
<212> TYPE: DNA
<213> ORGANISM: Artificial Sequence
<220> FEATURE:
<223> OTHER INFORMATION: Synthetic sequence

<400> SEQUENCE: 7

```
tgcggccgca agcttttatt tcagttcaat aatggtttcg                           40
```

<210> SEQ ID NO 8
<211> LENGTH: 33
<212> TYPE: DNA
<213> ORGANISM: Artificial Sequence
<220> FEATURE:
<223> OTHER INFORMATION: Synthetic sequence

<400> SEQUENCE: 8
tatgagctcc aaagaggtga tgaggatcct caa                                    33

<210> SEQ ID NO 9
<211> LENGTH: 35
<212> TYPE: DNA
<213> ORGANISM: Artificial Sequence
<220> FEATURE:
<223> OTHER INFORMATION: Synthetic sequence

<400> SEQUENCE: 9
tataagcttt cagagtttga gtaagccaaa agatg                                  35

<210> SEQ ID NO 10
<211> LENGTH: 35
<212> TYPE: DNA
<213> ORGANISM: Artificial Sequence
<220> FEATURE:
<223> OTHER INFORMATION: Synthetic sequence

<400> SEQUENCE: 10
ctatacaaag atgctgacgg tgtatatgtg tctgc                                  35

<210> SEQ ID NO 11
<211> LENGTH: 24
<212> TYPE: DNA
<213> ORGANISM: Artificial Sequence
<220> FEATURE:
<223> OTHER INFORMATION: Synthetic sequence

<400> SEQUENCE: 11
cggatcctgg ctgtggtgat gatg                                              24

<210> SEQ ID NO 12
<211> LENGTH: 34
<212> TYPE: DNA
<213> ORGANISM: Artificial Sequence
<220> FEATURE:
<223> OTHER INFORMATION: Synthetic sequence

<400> SEQUENCE: 12
gtgtctgcgc ttccgattaa agctatcaaa tacg                                   34

<210> SEQ ID NO 13
<211> LENGTH: 148
<212> TYPE: PRT
<213> ORGANISM: Homo sapiens

<400> SEQUENCE: 13

Gln Lys Gly Asp Gln Asn Pro Gln Ile Ala Ala His Val Ile Ser Glu
1               5                   10                  15

Ala Ser Ser Lys Thr Thr Ser Val Leu Gln Trp Ala Glu Lys Gly Tyr
            20                  25                  30

Tyr Thr Met Ser Asn Asn Leu Val Thr Leu Glu Asn Gly Lys Gln Leu
        35                  40                  45

Thr Val Lys Arg Gln Gly Leu Tyr Tyr Ile Tyr Ala Gln Val Thr Phe
    50                  55                  60

```
Cys Ser Asn Arg Glu Ala Ser Ser Gln Ala Pro Phe Ile Ala Ser Leu
 65                  70                  75                  80

Cys Leu Lys Ser Pro Gly Arg Phe Glu Arg Ile Leu Leu Arg Ala Ala
                 85                  90                  95

Asn Thr His Ser Ser Ala Lys Pro Cys Gly Gln Gln Ser Ile His Leu
            100                 105                 110

Gly Gly Val Phe Glu Leu Gln Pro Gly Ala Ser Val Phe Val Asn Val
            115                 120                 125

Thr Asp Pro Ser Gln Val Ser His Gly Thr Gly Phe Thr Ser Phe Gly
        130                 135                 140

Leu Leu Lys Leu
145

<210> SEQ ID NO 14
<211> LENGTH: 243
<212> TYPE: PRT
<213> ORGANISM: Homo sapiens

<400> SEQUENCE: 14

Thr Asn Glu Leu Lys Gln Met Gln Asp Lys Tyr Ser Lys Ser Gly Ile
 1               5                  10                  15

Ala Cys Phe Leu Lys Glu Asp Asp Ser Tyr Trp Asp Pro Asn Asp Glu
                 20                  25                  30

Glu Ser Met Asn Ser Pro Cys Trp Gln Val Lys Trp Gln Leu Arg Gln
             35                  40                  45

Leu Val Arg Lys Met Ile Leu Arg Thr Ser Glu Glu Thr Ile Ser Thr
 50                  55                  60

Val Gln Glu Lys Gln Gln Asn Ile Ser Pro Leu Val Arg Glu Arg Gly
 65                  70                  75                  80

Pro Gln Arg Val Ala Ala His Ile Thr Gly Thr Arg Gly Arg Ser Asn
                 85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
            115                 120                 125

Leu His Leu Arg Asn Gly Glu Leu Val Ile His Glu Lys Gly Phe Tyr
        130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
        195                 200                 205

Ile Phe Glu Leu Lys Glu Asn Asp Arg Ile Phe Val Ser Val Thr Asn
        210                 215                 220

Glu His Leu Ile Asp Met Asp His Glu Ala Ser Phe Phe Gly Ala Phe
225                 230                 235                 240

Leu Val Gly

<210> SEQ ID NO 15
<211> LENGTH: 168
<212> TYPE: PRT
<213> ORGANISM: Homo sapiens
```

-continued

```
<400> SEQUENCE: 15

Val Arg Glu Arg Gly Pro Gln Arg Val Ala His Ile Thr Gly Thr
1               5                   10                  15

Arg Gly Arg Ser Asn Thr Leu Ser Ser Pro Asn Ser Lys Asn Glu Lys
                20                  25                  30

Ala Leu Gly Arg Lys Ile Asn Ser Trp Glu Ser Ser Arg Ser Gly His
            35                  40                  45

Ser Phe Leu Ser Asn Leu His Leu Arg Asn Gly Glu Leu Val Ile His
        50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 16
<211> LENGTH: 150
<212> TYPE: PRT
<213> ORGANISM: Mus musculus

<400> SEQUENCE: 16

Lys Gln Gln Gln Arg Leu Leu Glu His Pro Glu Pro His Thr Ala Glu
1               5                   10                  15

Leu Gln Leu Asn Leu Thr Val Pro Arg Lys Asp Pro Thr Leu Arg Trp
                20                  25                  30

Gly Ala Gly Pro Ala Leu Gly Arg Ser Phe Thr His Gly Pro Glu Leu
            35                  40                  45

Glu Glu Gly His Leu Arg Ile His Gln Asp Gly Leu Tyr Arg Leu His
        50                  55                  60

Ile Gln Val Thr Leu Ala Asn Cys Ser Ser Pro Gly Ser Thr Leu Gln
65                  70                  75                  80

His Arg Ala Thr Leu Ala Val Gly Ile Cys Ser Pro Ala Ala His Gly
                85                  90                  95

Ile Ser Leu Leu Arg Gly Arg Phe Gly Gln Asp Cys Thr Val Ala Leu
            100                 105                 110

Gln Arg Leu Thr Tyr Leu Val His Gly Asp Val Leu Cys Thr Asn Leu
        115                 120                 125

Thr Leu Pro Leu Leu Pro Ser Arg Asn Ala Asp Glu Thr Phe Phe Gly
    130                 135                 140

Val Gln Trp Ile Cys Pro
145                 150

<210> SEQ ID NO 17
<211> LENGTH: 206
<212> TYPE: PRT
<213> ORGANISM: Mus musculus
```

<400> SEQUENCE: 17

Arg Thr Glu Pro Arg Pro Ala Leu Thr Ile Thr Thr Ser Pro Asn Leu
1               5                   10                  15

Gly Thr Arg Glu Asn Asn Ala Asp Gln Val Thr Pro Val Ser His Ile
            20                  25                  30

Gly Cys Pro Asn Thr Thr Gln Gln Gly Ser Pro Val Phe Ala Lys Leu
        35                  40                  45

Leu Ala Lys Asn Gln Ala Ser Leu Cys Asn Thr Thr Leu Asn Trp His
    50                  55                  60

Ser Gln Asp Gly Ala Gly Ser Ser Tyr Leu Ser Gln Gly Leu Arg Tyr
65                  70                  75                  80

Glu Glu Asp Lys Lys Glu Leu Val Val Asp Ser Pro Gly Leu Tyr Tyr
                85                  90                  95

Val Phe Leu Glu Leu Lys Leu Ser Pro Thr Phe Thr Asn Thr Gly His
            100                 105                 110

Lys Val Gln Gly Trp Val Ser Leu Val Leu Gln Ala Lys Pro Gln Val
            115                 120                 125

Asp Asp Phe Asp Asn Leu Ala Leu Thr Val Glu Leu Phe Pro Cys Ser
        130                 135                 140

Met Glu Asn Lys Leu Val Asp Arg Ser Trp Ser Gln Leu Leu Leu Leu
145                 150                 155                 160

Lys Ala Gly His Arg Leu Ser Val Gly Leu Arg Ala Tyr Leu His Gly
                165                 170                 175

Ala Gln Asp Ala Tyr Arg Asp Trp Glu Leu Ser Tyr Pro Asn Thr Thr
            180                 185                 190

Ser Phe Gly Leu Phe Leu Val Lys Pro Asp Asn Pro Trp Glu
        195                 200                 205

<210> SEQ ID NO 18
<211> LENGTH: 130
<212> TYPE: PRT
<213> ORGANISM: Mus musculus

<400> SEQUENCE: 18

Leu Lys Pro Thr Ala Ile Glu Ser Cys Met Val Lys Phe Glu Leu Ser
1               5                   10                  15

Ser Ser Lys Trp His Met Thr Ser Pro Lys Pro His Cys Val Asn Thr
            20                  25                  30

Thr Ser Asp Gly Lys Leu Lys Ile Leu Gln Ser Gly Thr Tyr Leu Ile
        35                  40                  45

Tyr Gly Gln Val Ile Pro Val Asp Lys Lys Tyr Ile Lys Asp Asn Ala
    50                  55                  60

Pro Phe Val Val Gln Ile Tyr Lys Lys Asn Asp Val Leu Gln Thr Leu
65                  70                  75                  80

Met Asn Asp Phe Gln Ile Leu Pro Ile Gly Gly Val Tyr Glu Leu His
                85                  90                  95

Ala Gly Asp Asn Ile Tyr Leu Lys Phe Asn Ser Lys Asp His Ile Gln
            100                 105                 110

Lys Thr Asn Thr Tyr Trp Gly Ile Ile Leu Met Pro Asp Leu Pro Phe
            115                 120                 125

Ile Ser
    130

<210> SEQ ID NO 19
<211> LENGTH: 402
<212> TYPE: PRT
<213> ORGANISM: Artificial Sequence
<220> FEATURE:
<223> OTHER INFORMATION: Synthetic sequence

<400> SEQUENCE: 19

```
Met Gly Ser Ser His His His His His Ser Leu Val Pro Arg Gly
1               5                   10                  15

Ser Gln Asp Pro Met Ala Asn Pro Asn Phe Thr Pro Ser Trp Pro Leu
            20                  25                  30

Tyr Lys Asp Ala Asp Gly Val Tyr Val Ser Ala Leu Pro Ile Lys Ala
        35                  40                  45

Ile Lys Tyr Ala Asn Asp Gly Ser Ala Asn Ala Glu Phe Asp Gly Pro
    50                  55                  60

Tyr Ala Asp Gln Tyr Met Ser Ala Gln Thr Val Ala Val Phe Lys Pro
65                  70                  75                  80

Glu Val Gly Gly Tyr Leu Phe Arg Ser Gln Tyr Gly Glu Leu Leu Tyr
                85                  90                  95

Met Ser Lys Thr Ala Phe Glu Ala Asn Tyr Thr Ser Ala Ser Gly Ser
            100                 105                 110

Val Ala Asn Ala Glu Thr Ala Asp Lys Leu Ser Thr Ala Arg Thr Ile
        115                 120                 125

Thr Leu Thr Gly Ala Val Thr Gly Ser Ala Ser Phe Asp Gly Ser Ala
    130                 135                 140

Asn Val Thr Ile Glu Thr Thr Ser Gly Ser Gly Ser Ser Gly Ser Thr
145                 150                 155                 160

Asn Glu Leu Lys Gln Met Gln Asp Lys Tyr Ser Lys Ser Gly Ile Ala
                165                 170                 175

Cys Phe Leu Lys Glu Asp Asp Ser Tyr Trp Asp Pro Asn Asp Glu Glu
            180                 185                 190

Ser Met Asn Ser Pro Cys Trp Gln Val Lys Trp Gln Leu Arg Gln Leu
        195                 200                 205

Val Arg Lys Met Ile Leu Arg Thr Ser Glu Glu Thr Ile Ser Thr Val
    210                 215                 220

Gln Glu Lys Gln Gln Asn Ile Ser Pro Leu Val Arg Glu Arg Gly Pro
225                 230                 235                 240

Gln Arg Val Ala Ala His Ile Thr Gly Thr Arg Gly Arg Ser Asn Thr
                245                 250                 255

Leu Ser Ser Pro Asn Ser Lys Asn Glu Lys Ala Leu Gly Arg Lys Ile
            260                 265                 270

Asn Ser Trp Glu Ser Ser Arg Ser Gly His Ser Phe Leu Ser Asn Leu
        275                 280                 285

His Leu Arg Asn Gly Glu Leu Val Ile His Glu Lys Gly Phe Tyr Tyr
    290                 295                 300

Ile Tyr Ser Gln Thr Tyr Phe Arg Phe Gln Glu Glu Ile Lys Glu Asn
305                 310                 315                 320

Thr Lys Asn Asp Lys Gln Met Val Gln Tyr Ile Tyr Lys Tyr Thr Ser
                325                 330                 335

Tyr Pro Asp Pro Ile Leu Leu Met Lys Ser Ala Arg Asn Ser Cys Trp
            340                 345                 350

Ser Lys Asp Ala Glu Tyr Gly Leu Tyr Ser Ile Tyr Gln Gly Gly Ile
        355                 360                 365
```

```
Phe Glu Leu Lys Glu Asn Asp Arg Ile Phe Val Ser Val Thr Asn Glu
        370                 375                 380

His Leu Ile Asp Met Asp His Glu Ala Ser Phe Phe Gly Ala Phe Leu
385                 390                 395                 400

Val Gly
```

<210> SEQ ID NO 20
<211> LENGTH: 1209
<212> TYPE: DNA
<213> ORGANISM: Artificial Sequence
<220> FEATURE:
<223> OTHER INFORMATION: Synthetic sequence

<400> SEQUENCE: 20

```
atgggcagca gccatcacca ccatcaccac agcctcgtcc cgcgcggctc acaggatccc      60
atggcaaacc caaacttcac gccatcatgg cctctataca aagatgctga cggtgtatat     120
gtgtctgcgc ttccgattaa agctatcaaa tacgctaatg acggaagtgc aaacgcagaa     180
ttcgacggcc cgtatgctga ccagtacatg tcagcgcaaa cagtagccgt attcaagccg     240
gaggttggcg atatctgtt ccggagccag tacggcgagc tgctctatat gagcaagaca     300
gcatttgaag ctaactacac ttctgcaagc ggttcagtag ctaatgcaga cggcggat      360
aagttatcta ctgcccgcac tatcacacta accggagcgg tcacaggttc agcgtccttt     420
gatggttcgg ctaacgtgac tatcgaaaca acatcaggaa gtggatcctc aggttcaacg     480
aacgagttga acaaatgca agacaagtat tctaaaagtg gcattgcgtg cttcttgaaa     540
gaagacgata gctactggga cccaaatgac gaggagtcca tgaattcacc ttgttggcag     600
gtaaaatggc aactgcgtca attggttcgt aaaatgatcc tgcgtacctc agaggagacg     660
attagcacag tgcaggagaa gcaacagaat atctcgccac tggtccgcga acgtgggccc     720
caacgtgttg ctgcccacat tacaggcact cgtggacgct ctaacacttt atcttcgcct     780
aactccaaaa atgaaaaggc gttgggtcgc aaaatcaatt cctgggaatc ctcccgttca     840
gggcacagtt tcttgagcaa ccttcacctt cgtaacggtg agcttgtcat ccacgagaag     900
ggatttttact acatctatag ccagacatat ttccgctttc aagaagagat taaggaaaac     960
actaaaaatg acaaacaaat ggtgcagtat atctataaat atactagtta tcccgatcca    1020
attcttctta tgaaaagtgc gcgtaactcg tgctggagta aggacgccga gtatggcttg    1080
tactctattt accaaggagg tattttttgag ttaaaagaga acgatcgtat ctttgttcc    1140
gtaacaaacg agcacttgat cgacatggat catgaagcta gtttctttgg agctttttta    1200
gtggggtaa                                                            1209
```

<210> SEQ ID NO 21
<211> LENGTH: 310
<212> TYPE: PRT
<213> ORGANISM: Artificial Sequence
<220> FEATURE:
<223> OTHER INFORMATION: Synthetic sequence

<400> SEQUENCE: 21

```
Met Gly Ser Ser His His His His His His Ser Leu Val Pro Arg Gly
1               5                   10                  15

Ser Gln Asp Pro Met Ala Asn Pro Asn Phe Thr Pro Ser Trp Pro Leu
            20                  25                  30

Tyr Lys Asp Ala Asp Gly Val Tyr Val Ser Ala Leu Pro Ile Lys Ala
        35                  40                  45
```

Ile Lys Tyr Ala Asn Asp Gly Ser Ala Asn Ala Glu Phe Asp Gly Pro
 50                  55                  60

Tyr Ala Asp Gln Tyr Met Ser Ala Gln Thr Val Ala Val Phe Lys Pro
 65                  70                  75                  80

Glu Val Gly Gly Tyr Leu Phe Arg Ser Gln Tyr Gly Glu Leu Leu Tyr
                 85                  90                  95

Met Ser Lys Thr Ala Phe Glu Ala Asn Tyr Thr Ser Ala Ser Gly Ser
            100                 105                 110

Val Ala Asn Ala Glu Thr Ala Asp Lys Leu Ser Thr Ala Arg Thr Ile
            115                 120                 125

Thr Leu Thr Gly Ala Val Thr Gly Ser Ala Ser Phe Asp Gly Ser Ala
130                 135                 140

Asn Val Thr Ile Glu Thr Thr Ser Gly Ser Gly Ser Ser Gly Ser Ser
145                 150                 155                 160

Lys Gln Gln Gln Arg Leu Leu Glu His Pro Glu Pro His Thr Ala Glu
                165                 170                 175

Leu Gln Leu Asn Leu Thr Val Pro Arg Lys Asp Pro Thr Leu Arg Trp
            180                 185                 190

Gly Ala Gly Pro Ala Leu Gly Arg Ser Phe Thr His Gly Pro Glu Leu
            195                 200                 205

Glu Glu Gly His Leu Arg Ile His Gln Asp Gly Leu Tyr Arg Leu His
210                 215                 220

Ile Gln Val Thr Leu Ala Asn Cys Ser Ser Pro Gly Ser Thr Leu Gln
225                 230                 235                 240

His Arg Ala Thr Leu Ala Val Gly Ile Cys Ser Pro Ala Ala His Gly
                245                 250                 255

Ile Ser Leu Leu Arg Gly Arg Phe Gly Gln Asp Cys Thr Val Ala Leu
            260                 265                 270

Gln Arg Leu Thr Tyr Leu Val His Gly Asp Val Leu Cys Thr Asn Leu
            275                 280                 285

Thr Leu Pro Leu Leu Pro Ser Arg Asn Ala Asp Glu Thr Phe Phe Gly
            290                 295                 300

Val Gln Trp Ile Cys Pro
305                 310

<210> SEQ ID NO 22
<211> LENGTH: 933
<212> TYPE: DNA
<213> ORGANISM: Artificial Sequence
<220> FEATURE:
<223> OTHER INFORMATION: Synthetic sequence

<400> SEQUENCE: 22
atgggcagca gccatcacca ccatcaccac agcctcgtcc cgcgcggctc acaggatccc     60
atggcaaacc caaacttcac gccatcatgg cctctataca agatgctga cggtgtatat    120 gtgtctgcgc ttccgattaa agctatcaaa tacgctaatg acggaagtgc aaacgcagaa    180
ttcgacggcc cgtatgctga ccagtacatg tcagcgcaaa cagtagccgt attcaagccg    240
gaggttggcg gatatctgtt ccggagccag tacggcgagc tgctctatat gagcaagaca    300
gcatttgaag ctaactacac ttctgcaagc ggttcagtag ctaatgcaga cggcggat    360 aagttatcta ctgcccgcac tatcacacta accggagcgg tcacaggttc agcgtccttt    420
gatggttcgg ctaacgtgac tatcgaaaca acatcaggaa gtggatccag tggctcttct    480
aagcaacaac aacgtttgtt ggagcaccca gaacctcaca ctgccgagct gcaactgaat    540

-continued

```
ttaacagtac cacgtaagga cccaacgtta cgttggggag ccggcccagc gttaggtcgc    600
tcttttactc acggccctga attagaggag ggtcacctgc gtattcacca agacggcttg    660
taccgtctgc atatccaggt aacgttggct aactgttcat ctccgggttc gaccttacag    720
caccgcgcaa cactggctgt agggatctgc tccctgccg ctcacgggat tagtctgctt    780
cgcgggcgtt ttggtcaaga ttgcactgta gcattacaac gtcttactta tttagtacac    840
ggtgacgtcc tgtgtaccaa cttgacgtta cctcttctgc cttcccgtaa cgcagatgag    900
actttctttg gcgtccagtg gatctgcccc taa                                 933
```

<210> SEQ ID NO 23
<211> LENGTH: 365
<212> TYPE: PRT
<213> ORGANISM: Artificial Sequence
<220> FEATURE:
<223> OTHER INFORMATION: Synthetic sequence

<400> SEQUENCE: 23

```
Met Gly Ser Ser His His His His His Ser Leu Val Pro Arg Gly
  1               5                  10                  15

Ser Gln Asp Pro Met Ala Asn Pro Asn Phe Thr Pro Ser Trp Pro Leu
             20                  25                  30

Tyr Lys Asp Ala Asp Gly Val Tyr Val Ser Ala Leu Pro Ile Lys Ala
         35                  40                  45

Ile Lys Tyr Ala Asn Asp Gly Ser Ala Asn Ala Glu Phe Asp Gly Pro
     50                  55                  60

Tyr Ala Asp Gln Tyr Met Ser Ala Gln Thr Val Ala Val Phe Lys Pro
 65                  70                  75                  80

Glu Val Gly Gly Tyr Leu Phe Arg Ser Gln Tyr Gly Glu Leu Leu Tyr
                 85                  90                  95

Met Ser Lys Thr Ala Phe Glu Ala Asn Tyr Thr Ser Ala Ser Gly Ser
            100                 105                 110

Val Ala Asn Ala Glu Thr Ala Asp Lys Leu Ser Thr Ala Arg Thr Ile
        115                 120                 125

Thr Leu Thr Gly Ala Val Thr Gly Ser Ala Ser Phe Asp Gly Ser Ala
    130                 135                 140

Asn Val Thr Ile Glu Thr Thr Ser Gly Ser Gly Ser Ser Gly Ser Arg
145                 150                 155                 160

Thr Glu Pro Arg Pro Ala Leu Thr Ile Thr Thr Ser Pro Asn Leu Gly
                165                 170                 175

Thr Arg Glu Asn Asn Ala Asp Gln Val Thr Pro Val Ser His Ile Gly
            180                 185                 190

Cys Pro Asn Thr Thr Gln Gln Gly Ser Pro Val Phe Ala Lys Leu Leu
        195                 200                 205

Ala Lys Asn Gln Ala Ser Leu Cys Asn Thr Thr Leu Asn Trp His Ser
    210                 215                 220

Gln Asp Gly Ala Gly Ser Ser Tyr Leu Ser Gln Gly Leu Arg Tyr Glu
225                 230                 235                 240

Glu Asp Lys Lys Glu Leu Val Val Asp Ser Pro Gly Leu Tyr Tyr Val
                245                 250                 255

Phe Leu Glu Leu Lys Leu Ser Pro Thr Phe Thr Asn Thr Gly His Lys
            260                 265                 270

Val Gln Gly Trp Val Ser Leu Val Leu Gln Ala Lys Pro Gln Val Asp
        275                 280                 285
```

```
Asp Phe Asp Asn Leu Ala Leu Thr Val Glu Leu Phe Pro Cys Ser Met
    290                 295                 300

Glu Asn Lys Leu Val Asp Arg Ser Trp Ser Gln Leu Leu Leu Leu Lys
305                 310                 315                 320

Ala Gly His Arg Leu Ser Val Gly Leu Arg Ala Tyr Leu His Gly Ala
                325                 330                 335

Gln Asp Ala Tyr Arg Asp Trp Glu Leu Ser Tyr Pro Asn Thr Thr Ser
                340                 345                 350

Phe Gly Leu Phe Leu Val Lys Pro Asp Asn Pro Trp Glu
            355                 360                 365

<210> SEQ ID NO 24
<211> LENGTH: 1098
<212> TYPE: DNA
<213> ORGANISM: Artificial Sequence
<220> FEATURE:
<223> OTHER INFORMATION: Synthetic sequence

<400> SEQUENCE: 24
atgggcagca gccatcacca ccatcaccac agcctcgtcc cgcgcggctc acaggatccc      60
atggcaaacc caaacttcac gccatcatgg cctctataca agatgctga cggtgtatat     120 gtgtctgcgc ttccgattaa agctatcaaa tacgctaatg acggaagtgc aaacgcagaa     180
ttcgacggcc gtatgctga ccagtacatg tcagcgcaaa cagtagccgt attcaagccg     240
gaggttggcg atatctgtt ccggagccag tacggcgagc tgctctatat gagcaagaca     300
gcatttgaag ctaactacac ttctgcaagc ggttcagtag ctaatgcaga dcggcggat     360 aagttatcta ctgcccgcac tatcacacta accggagcgg tcacaggttc agcgtccttt     420
gatggttcgg ctaacgtgac tatcgaaaca catcaggaa gtggatcctc gggaagtcgc     480
actgaacctc gccccgctct gaccatcacg acaagcccga atctgggtac cgcgaaaat     540 aacgcagatc aggtaacccc ggtatcccac attggttgcc ctaatactac ccagcaagga     600
agtccggtct ttgcaaaact tcttgctaaa accaagcct ccttatgcaa caccacgctt     660
aattggcatt cccaagacgg agcagggtct agctacttgt tcagggcct gcgttacgag     720 gaagataaga aggaattggt ggttgactct cctggcctgt actacgtgtt cttggagctt     780
aaactgagcc ctacgttcac gaatacaggt cacaaagttc aaggatgggt ctctttggtt     840
ttacaggcta aacctcaagt cgacgacttt gataatctgg ctttaaccgt ggagttattc     900
ccgtgtagta tggagaacaa gttggtggat cgtagctggt cgcaactgct gcttcttaaa     960
gcgggacacc gtctgtcagt gggtctgcgt gcctacttac atggcgctca agatgcctat    1020
cgcgactggg aattaagcta cccgaacacc acatcgttcg ggttgttcct tgtcaaacct    1080 gacaacccttt gggagtaa                                                  1098

<210> SEQ ID NO 25
<211> LENGTH: 291
<212> TYPE: PRT
<213> ORGANISM: Artificial Sequence
<220> FEATURE:
<223> OTHER INFORMATION: Synthetic sequence

<400> SEQUENCE: 25

Met Gly Ser Ser His His His His His His Ser Leu Val Pro Arg Gly
1               5                   10                  15

Ser Gln Asp Pro Met Ala Asn Pro Asn Phe Thr Pro Ser Trp Pro Leu
            20                  25                  30
```

```
Tyr Lys Asp Ala Asp Gly Val Tyr Val Ser Ala Leu Pro Ile Lys Ala
            35                  40                  45
Ile Lys Tyr Ala Asn Asp Gly Ser Ala Asn Ala Glu Phe Asp Gly Pro
 50                  55                  60
Tyr Ala Asp Gln Tyr Met Ser Ala Gln Thr Val Ala Val Phe Lys Pro
 65                  70                  75                  80
Glu Val Gly Gly Tyr Leu Phe Arg Ser Gln Tyr Gly Glu Leu Leu Tyr
                85                  90                  95
Met Ser Lys Thr Ala Phe Glu Ala Asn Tyr Thr Ser Ala Ser Gly Ser
            100                 105                 110
Val Ala Asn Ala Glu Thr Ala Asp Lys Leu Ser Thr Ala Arg Thr Ile
            115                 120                 125
Thr Leu Thr Gly Ala Val Thr Gly Ser Ala Ser Phe Asp Gly Ser Ala
130                 135                 140
Asn Val Thr Ile Glu Thr Thr Ser Gly Ser Gly Ser Ser Gly Ser Thr
145                 150                 155                 160
Ser Leu Lys Pro Thr Ala Ile Glu Ser Cys Met Val Lys Phe Glu Leu
                165                 170                 175
Ser Ser Ser Lys Trp His Met Thr Ser Pro Lys Pro His Cys Val Asn
            180                 185                 190
Thr Thr Ser Asp Gly Lys Leu Lys Ile Leu Gln Ser Gly Thr Tyr Leu
        195                 200                 205
Ile Tyr Gly Gln Val Ile Pro Val Asp Lys Lys Tyr Ile Lys Asp Asn
        210                 215                 220
Ala Pro Phe Val Val Gln Ile Tyr Lys Lys Asn Asp Val Leu Gln Thr
225                 230                 235                 240
Leu Met Asn Asp Phe Gln Ile Leu Pro Ile Gly Val Tyr Glu Leu
                245                 250                 255
His Ala Gly Asp Asn Ile Tyr Leu Lys Phe Asn Ser Lys Asp His Ile
            260                 265                 270
Gln Lys Thr Asn Thr Tyr Trp Gly Ile Ile Leu Met Pro Asp Leu Pro
        275                 280                 285
Phe Ile Ser
    290

<210> SEQ ID NO 26
<211> LENGTH: 876
<212> TYPE: DNA
<213> ORGANISM: Artificial Sequence
<220> FEATURE:
<223> OTHER INFORMATION: Synthetic sequence

<400> SEQUENCE: 26
atgggcagca gccatcacca ccatcaccac agcctcgtcc cgcgcggctc acaggatccc      60
atggcaaacc caaacttcac gccatcatgg cctctataca aagatgctga cggtgtatat     120
gtgtctgcgc ttccgattaa agctatcaaa tacgctaatg acggaagtgc aaacgcagaa     180
ttcgacggcc cgtatgctga ccagtacatg tcagcgcaaa cagtagccgt attcaagccg     240
gaggttggcg gatatctgtt ccggagccag tacggcgagc tgctctatat gagcaagaca     300
gcatttgaag ctaactacac ttctgcaagc ggttcagtag ctaatgcaga cggcggat      360 aagttatcta ctgcccgcac tatcacacta accggagcgg tcacaggttc agcgtccttt     420
gatggttcgg ctaacgtgac tatcgaaaca acatcaggaa gtggatcctc gggcagtact     480
tcgttgaaac caacagcaat cgagagctgc atggtcaagt tcgagctgtc ttcatccaaa     540
```

```
tggcacatga cgtctcccaa gcctcattgc gtaaatacga cttctgacgg aaagttaaag    600
attttgcaat cggggaccta cttaatttac ggtcaagtga ttcccgttga taagaagtac    660
attaaagata atgccccgtt tgtggtgcag atttacaaga aaatgatgt attacagact     720 cttatgaacg attttcagat ccttcccatt ggtggagtgt atgagttgca tgcgggggac    780
aacatctatc ttaaatttaa ttccaaggac catatccaaa aaacaaatac ctactgggt    840 attattttaa tgccagactt gcctttcatt tcctaa                              876

<210> SEQ ID NO 27
<211> LENGTH: 327
<212> TYPE: PRT
<213> ORGANISM: Artificial Sequence
<220> FEATURE:
<223> OTHER INFORMATION: Synthetic sequence

<400> SEQUENCE: 27

Met Gly Ser Ser His His His His His His Ser Leu Val Pro Arg Gly
1               5                   10                  15

Ser Gln Asp Pro Met Ala Asn Pro Asn Phe Thr Pro Ser Trp Pro Leu
            20                  25                  30

Tyr Lys Asp Ala Asp Gly Val Tyr Val Ser Ala Leu Pro Ile Lys Ala
        35                  40                  45

Ile Lys Tyr Ala Asn Asp Gly Ser Ala Asn Ala Glu Phe Asp Gly Pro
    50                  55                  60

Tyr Ala Asp Gln Tyr Met Ser Ala Gln Thr Val Ala Val Phe Lys Pro
65                  70                  75                  80

Glu Val Gly Gly Tyr Leu Phe Arg Ser Gln Tyr Gly Glu Leu Leu Tyr
                85                  90                  95

Met Ser Lys Thr Ala Phe Glu Ala Asn Tyr Thr Ser Ala Ser Gly Ser
            100                 105                 110

Val Ala Asn Ala Glu Thr Ala Asp Lys Leu Ser Thr Ala Arg Thr Ile
        115                 120                 125

Thr Leu Thr Gly Ala Val Thr Gly Ser Ala Ser Phe Asp Gly Ser Ala
    130                 135                 140

Asn Val Thr Ile Glu Thr Thr Ser Gly Ser Gly Ser Ser Gly Ser Val
145                 150                 155                 160

Arg Glu Arg Gly Pro Gln Arg Val Ala Ala His Ile Thr Gly Thr Arg
                165                 170                 175

Gly Arg Ser Asn Thr Leu Ser Ser Pro Asn Ser Lys Asn Glu Lys Ala
            180                 185                 190

Leu Gly Arg Lys Ile Asn Ser Trp Glu Ser Ser Arg Ser Gly His Ser
        195                 200                 205

Phe Leu Ser Asn Leu His Leu Arg Asn Gly Glu Leu Val Ile His Glu
    210                 215                 220

Lys Gly Phe Tyr Tyr Ile Tyr Ser Gln Thr Tyr Phe Arg Phe Gln Glu
225                 230                 235                 240

Glu Ile Lys Glu Asn Thr Lys Asn Asp Lys Gln Met Val Gln Tyr Ile
                245                 250                 255

Tyr Lys Tyr Thr Ser Tyr Pro Asp Pro Ile Leu Leu Met Lys Ser Ala
            260                 265                 270

Arg Asn Ser Cys Trp Ser Lys Asp Ala Glu Tyr Gly Leu Tyr Ser Ile
        275                 280                 285

Tyr Gln Gly Gly Ile Phe Glu Leu Lys Glu Asn Asp Arg Ile Phe Val
    290                 295                 300
```

Ser Val Thr Asn Glu His Leu Ile Asp Met Asp His Glu Ala Ser Phe
305                 310                 315                 320

Phe Gly Ala Phe Leu Val Gly
            325

<210> SEQ ID NO 28
<211> LENGTH: 984
<212> TYPE: DNA
<213> ORGANISM: Artificial Sequence
<220> FEATURE:
<223> OTHER INFORMATION: Synthetic sequence

<400> SEQUENCE: 28

```
atgggcagca gccatcacca ccatcaccac agcctcgtcc cgcgcggctc acaggatccc      60
atggcaaacc caaacttcac gccatcatgg cctctataca aagatgctga cggtgtatat     120
gtgtctgcgc ttccgattaa agctatcaaa tacgctaatg acggaagtgc aaacgcagaa     180
ttcgacggcc cgtatgctga ccagtacatg tcagcgcaaa cagtagccgt attcaagccg     240
gaggttggcg gatatctgtt ccggagccag tacggcgagc tgctctatat gagcaagaca     300
gcatttgaag ctaactacac ttctgcaagc ggttcagtag ctaatgcaga gacggcggat     360
aagttatcta ctgcccgcac tatcacacta accggagcgg tcacaggttc agcgtccttt     420
gatggttcgg ctaacgtgac tatcgaaaca acatcaggaa gtggatcctc aggttcagtc     480
cgcgaacgtg ggccccaacg tgttgctgcc cacattacag gcactcgtgg acgctctaac     540
actttatctt cgcctaactc caaaaatgaa aaggcgttgg gtcgcaaaat caattcctgg     600
gaatcctccc gttcagggca cagtttcttg agcaaccttc accttcgtaa cggtgagctt     660
gtcatccacg agaagggatt ttactacatc tatagccaga catatttccg ctttcaagaa     720
gagattaagg aaaacactaa aaatgacaaa caaatggtgc agtatatcta taaatatact     780
agttatcccg atccaattct tcttatgaaa agtgcgcgta actcgtgctg gagtaaggac     840
gccgagtatg gcttgtactc tatttaccaa ggaggtattt ttgagttaaa agagaacgat     900
cgtatctttg tttccgtaac aaacgagcac ttgatcgaca tggatcatga agctagtttc     960
tttggagctt ttttagtggg gtaa                                            984
```

<210> SEQ ID NO 29
<211> LENGTH: 151
<212> TYPE: PRT
<213> ORGANISM: Artificial Sequence
<220> FEATURE:
<223> OTHER INFORMATION: Synthetic sequence

<400> SEQUENCE: 29

Met Gly Ser Ser His His His His His His Ser Leu Val Pro Arg Gly
1               5                   10                  15

Ser Gln Asp Pro Met Ala Asn Pro Asn Phe Thr Pro Ser Trp Pro Leu
            20                  25                  30

Tyr Lys Asp Ala Asp Gly Val Tyr Val Ser Ala Leu Pro Ile Lys Ala
        35                  40                  45

Ile Lys Tyr Ala Asn Asp Gly Ser Ala Asn Ala Glu Phe Asp Gly Pro
    50                  55                  60

Tyr Ala Asp Gln Tyr Met Ser Ala Gln Thr Val Ala Val Phe Lys Pro
65                  70                  75                  80

Glu Val Gly Gly Tyr Leu Phe Arg Ser Gln Tyr Gly Glu Leu Leu Tyr
                85                  90                  95

```
Met Ser Lys Thr Ala Phe Glu Ala Asn Tyr Thr Ala Ser Gly Ser
            100                 105                 110

Val Ala Asn Ala Glu Thr Ala Asp Lys Leu Ser Thr Arg Thr Ile
        115                 120                 125

Thr Leu Thr Gly Ala Val Thr Gly Ser Ala Ser Phe Asp Gly Ser Ala
    130                 135                 140

Asn Val Thr Ile Glu Thr Thr
145                 150

<210> SEQ ID NO 30
<211> LENGTH: 141
<212> TYPE: PRT
<213> ORGANISM: Artificial Sequence
<220> FEATURE:
<223> OTHER INFORMATION: Synthetic sequence

<400> SEQUENCE: 30

Ser Leu Val Pro Arg Gly Ser Gln Asp Pro Met Ala Asn Pro Asn Phe
1               5                   10                  15

Thr Pro Ser Trp Pro Leu Tyr Lys Asp Ala Asp Gly Val Tyr Val Ser
            20                  25                  30

Ala Leu Pro Ile Lys Ala Ile Lys Tyr Ala Asn Asp Gly Ser Ala Asn
        35                  40                  45

Ala Glu Phe Asp Gly Pro Tyr Ala Asp Gln Tyr Met Ser Ala Gln Thr
    50                  55                  60

Val Ala Val Phe Lys Pro Glu Val Gly Gly Tyr Leu Phe Arg Ser Gln
65                  70                  75                  80

Tyr Gly Glu Leu Leu Tyr Met Ser Lys Thr Ala Phe Glu Ala Asn Tyr
                85                  90                  95

Thr Ser Ala Ser Gly Ser Val Ala Asn Ala Glu Thr Ala Asp Lys Leu
            100                 105                 110

Ser Thr Ala Arg Thr Ile Thr Leu Thr Gly Ala Val Thr Gly Ser Ala
        115                 120                 125

Ser Phe Asp Gly Ser Ala Asn Val Thr Ile Glu Thr Thr
    130                 135                 140

<210> SEQ ID NO 31
<211> LENGTH: 31
<212> TYPE: DNA
<213> ORGANISM: Artificial Sequence
<220> FEATURE:
<223> OTHER INFORMATION: Synthetic sequence

<400> SEQUENCE: 31
gagctcggcg cgcctgcagg tcgacaagct t                           31

<210> SEQ ID NO 32
<211> LENGTH: 31
<212> TYPE: DNA
<213> ORGANISM: Artificial Sequence
<220> FEATURE:
<223> OTHER INFORMATION: Synthetic sequence

<400> SEQUENCE: 32
ggatccactt cctgatgttg tttcgatagt c                           31
```

PRESENTATION OF BIOACTIVE PROTEINS

CROSS-REFERENCE TO RELATED APPLICATIONS

This patent application claims the benefit of U.S. Provisional Application No. 62/331,869, filed May 4, 2016, which is incorporated herein by reference in its entirety for all purposes.

STATEMENT REGARDING FEDERALLY SPONSORED RESEARCH AND DEVELOPMENT

This invention was made with Government support under Grant Number AI104905 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 41,274 Byte ASCII (Text) file named "728612_ST25.TXT," created on May 5, 2017.

BACKGROUND OF THE INVENTION

The Tumor Necrosis Factor Super Family (TNFSF) consists of approximately 20 cellular surface signaling proteins with a conserved trimeric structure. All members of the TNFSF perform key roles in the activation or control of the immune system. The main hurdle preventing clinical use of these proteins as adjuvants or direct therapies in diseases such as cancer has been the structural requirements for effective signaling.

CD40L is an example of a TNFSF family member. In its native signaling environment CD40L engages CD40 on the surface of an adjacent cell to initiate signaling. CD40 initially adopts a monomeric structure on the cell surface, which is then trimerized by three CD40 subunits binding the three binding sites of the CD40L trimer. This in turn allows the cytosolic region of CD40 to engage the trimeric TRAF receptors, which serve as signal mediators for many of the TNFSF members. In addition to the trimeric structure of the TNFSF members, robust signaling is also enabled by multiple CD40L-CD40 contacts adjacent to each other forming a cluster. This naturally occurs when two cells engage each other but does not occur if soluble CD40L is administered.

Currently therapeutic TNFSF protein (e.g., CD40L) administration is limited by the high dose needed to elicit a beneficial effect, which leads to toxic off target effects. Antibodies against TNFSF proteins, such as anti-CD40 antibodies, have been constructed to act as high affinity substitutes that bypass the need for polyvalent high avidity contacts. However these antibodies cannot crosslink in the correct trimeric structure for signaling unless the concentration of antibody is significantly high.

Therefore, there is a desire for products and methods for the display of trimeric proteins.

BRIEF SUMMARY OF THE INVENTION

The invention provides a fusion protein comprising an antigen binding domain linked to a bacteriophage decoration protein (Dec). The invention also provides a polynucleotide comprising the fusion protein and a vector comprising the polynucleotide.

Additionally, the invention provides a composition comprising the fusion protein and a virus-like particle (VLP), and a method of treating a disease in a mammal comprising administering a therapeutically effective amount of the composition to the mammal.

The invention also provides a method of vaccinating against a disease comprising administering a composition comprising the fusion protein and a VLP encapsulating a protein (e.g., an antigenic protein, such as an influenza antigenic protein).

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

In FIG. 2A, SDS-PAGE analysis shows a single band for each Dec construct at the expected molecular weight after Ni-affinity chromatography. In FIG. 2B, calibrated analytical size-exclusion chromatography reveals that DecWT, DecΔ11, DecΔ20 and DecSelf all exist as trimers in solution. DecCD40L interacted with the column and was not analyzed.

FIGS. 3A-3G are schematics and graphs of experimental data illustrating the binding of Dec fusion proteins to the VLP. FIG. 3A is a representation of the Dec trimer showing the central pillar capped with a cluster of the C-termini. FIG. 3B depicts DecWT binding to EX P22 results in a particle molecular weight shift of 2.5 MDa and a retention time shift of 0.62 minutes as measured by SEC-MALS. FIG. 3C depicts DecCD40L incorporating the C3 symmetric mCD40L at the C-terminus allowing for maintenance of the quaternary structure of both components. FIG. 3D illustrates DecCD40L binding results in a retention shift of 0.73 minutes and molecular weight increase of 1.9 MDa. Only 0.8 equivalents of DecCD40L per available site could be bound and analyzed by MALS due to interactions between DecCD40L and the column. FIG. 3E depicts DecSelf incorporating a short monomeric peptide at the C-terminus. FIG. 3F illustrates that DecSelf shows a similar molecular weight increase (2.1 MDa) and retention shift (0.5 minutes) on binding. The DecCD40L representation utilizes PDB 1ALY. FIG. 3G is a table with values of the global particle molecular weight, radius of hydration and retention shift of P22 upon Dec binding measured by SEC coupled to MALS and QELS.

In FIG. 4A, P22-mCherry decorated with DecCD40L showed binding to primary B-lymphocytes while P22- mCherry and P22-mCherry decorated with DecWT show minimal difference from a PBS control. In FIG. 4B, P22-Cy7 decorated with DecSelf showed minimal association with splenocytes compared to naked P22-Cy7 when incubated at 37° C. (P=0.0006 P22-Cy7 vs. P22-Cy7+DecSelf; P=0.0001 P22-Cy7 vs. PBS). In FIG. 4C, incubation of the same samples at 4° C. results in similar patterns associated with adhesion to splenocytes (P=0.0002 P22-Cy7 vs. P22-Cy7+DecSelf; P=0.0002 P22-Cy7 vs. PBS). All error bars reflect one standard deviation.

FIGS. 6A-6E are graphs of experimental results illustrating the binding affinity of the fusion proteins for the VLP. DecWT binding, measured by SPR, reflects biphasic behavior and low nanomolar affinity. DecCD40L and DecSelf are minimally affected by C-terminal fusion. In FIG. 6A, DecWT binding kinetics demonstrate biphasic behavior and are well fit to a two-site model. Application of the fit results in a high-affinity site $K_D$ of 9.2 nM and a low-affinity site $K_D$ of 1502 nM. In FIG. 6B, two-site fit was applied to the same concentration dataset but with the tight site kd held at $3.2 \times 10^{-6}$ sec$^{-1}$ reflecting the results of the 4 hr dissociation experiments. In FIG. 6C, DecCD40L binding kinetics, measured by SPR, demonstrate biphasic behavior and are well fit by a two-site model. Fits resulted in a high-affinity site $K_D$ of 30.8 nM and a low-affinity site $K_D$ 1,421 nM. In FIG. 6D, DecSelf kinetics also were well fit by a two-site model resulting in a high-affinity site $K_D$ of 18.3 nM and a low-affinity site $K_D$ 146 nM. For all SPR sets a single representative concentration set is displayed with data shown in traces with fits overlaid. Each trace shows a binding sensorgram for a different concentration of Dec construct (1-1580 nM). FIG. 6E is a table of the SPR kinetic binding parameters of Dec constructs and truncations for a two-site binding model.

In FIG. 7A, DecΔ11 binding to EX P22 results in a 3.1 MDa increase in particle mass and a 0.6 min shift in retention time as measured by SEC-MALS. In FIG. 7B, DecΔ20 incubation with EX P22 resulted in no mass increase or retention shift. In FIG. 7C, DecΔ11 binding kinetics, measured by SPR (1-1580 nM), were in good agreement with a two-site model resulting in a high-affinity site $K_D$ of 4.8 nM and a low-affinity site $K_D$ of 155 nM. In FIG. 7D, DecΔ20 binding kinetics (31.6-31,600 nM) only showed mono-phasic behavior over the concentrations examined resulting in a single-site $K_D$ of 3.5 μM. Each trace in FIGS. 7C and 7D shows a sensorgram of a different Dec construct concentration. For all SPR sets a single representative concentration set is displayed with data shown in k traces with fits overlaid.

In FIG. 8A, an initial purification of P22 PC exhibits the emergence of a higher molecular weight peak by SEC-MALS in the presence of excess Dec. In FIG. 8B, following selective crosslinking of the binding population using a disulfide forming Dec mutant (DecS134C) the higher molecular weight peak is removed. In FIG. 8C, a TEM micrograph of PC sample prior to crosslinking shows well-formed particles in the presence of misformed particles. In FIG. 8D, a TEM micrograph of Dec crosslinking induced aggregate shows a high percentage of misformed particles. In FIG. 8E, the recovered supernatant after crosslinking shows nearly complete removal of the misformed particle population. All scale bars are 500 nm.

FIG. 10A depicts SDS-Page displaying a major band for DechCD40L at the expected molecular weight of 33 kDa. FIG. 10B depicts a Western blot analysis of DechCD40L bound to EX P22 and recovered by ultracentrifugation compared to P22 alone or an admixture of P22 and DecWT. At left of FIG. 10B is a coomasie-stained gel showing bands at the expected molecular weights for DechCD40L (33 kDa), P22 CP (46 kDa) and DecWT (15 kDa). The center gel of FIG. 10B is blotted with an anti-P22 polyclonal mixture and the right gel of FIG. 10B is blotted with an anti-Dec polyclonal mixture.

FIGS. 11A-11C illustrate that DechCD40L binds at the expected quasi 3-fold and true 3-fold sites. Additional density can be seen at the anticipated binding sites when cryo-EM reconstructions of the background EX P22 VLP (FIG. 11A) were compared to the DechCD40L decorated P22 VLP (FIG. 11B). When the reconstructions were overlapped (FIG. 11C), the additional density can be seen to have a 3-fold symmetric base with a central pillar extending away from the capsid surface and terminating in a poorly resolved globular head.

FIG. 12A is a graph depicting that a concentration-dependent response was observed for both shCD40L and DechCD40L as free trimers. FIG. 12B is a graph showing the magnitude of activation at a CD40L monomer concentration of 3 nM for (from left to right) shCD40L, DechCD40L, EX P22 VLP, and DechCD40L+EX P22. FIG. 12C depicts different ratios of DechCD40L to EX P22 (upper values) compared to the same ratios of shCD40L and EX P22 in an admixture control. Ratios lead to different polyvalent potentials from a capsid oversaturated low polyvalency state at low ratios to VLP-optimized state at ~60 trimers/capsid to a VLP-starved state at higher ratios. SEAP activity measurements are the result of a 20-hour incubation of 60,000 cells with the indicated concentration of CD40L followed by a 30 min development and measurement of the absorbance at 635 nm. All sample-sets were independently assayed in triplicate. All error bars indicate one standard deviation on the mean.

In FIG. 13A, the SDS-PAGE analysis shows major protein band in expected region (Molecular Weight of DechTRAIL-T is 36.2 kilodaltons) indicating that DechTRAIL-T remains soluble during and post purification. In FIG. 13B the SDS-PAGE analysis shows that after purification and ultracentrifugation that DechTRAIL-T remains bound to P22.

DETAILED DESCRIPTION OF THE INVENTION

Figure 1:
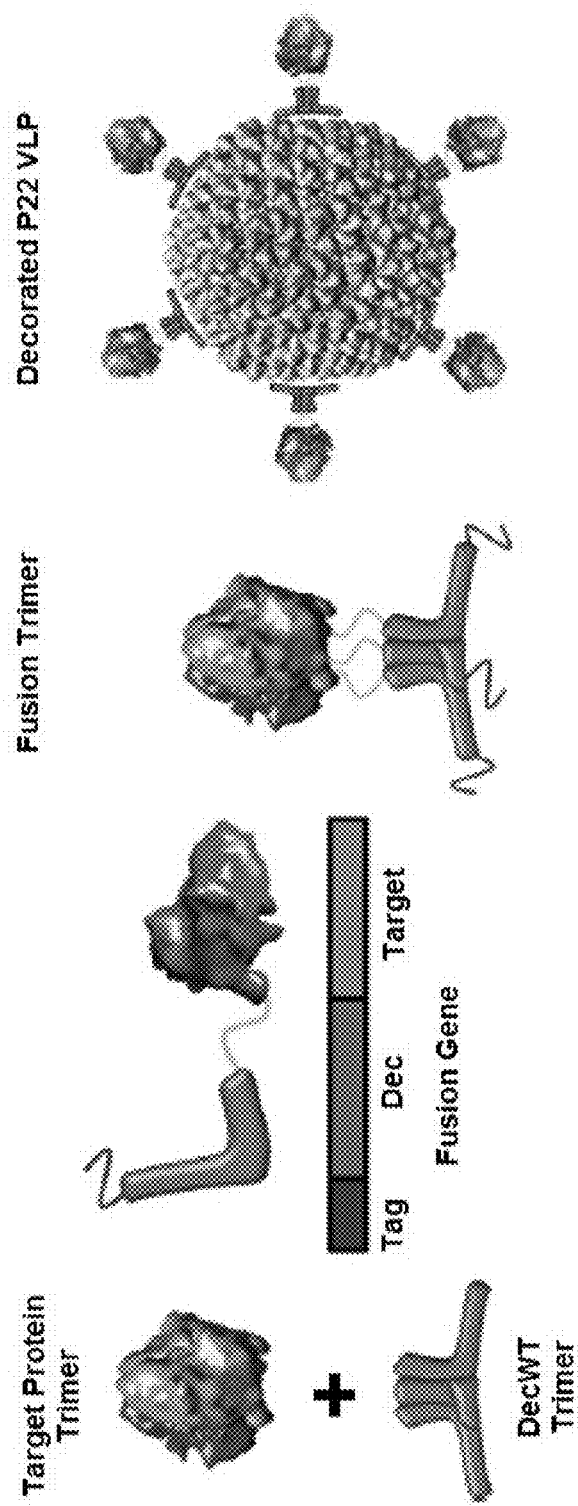
FIG. 1 is a schematic displaying the general strategy for polyvalent presentation mediated by Dec binding to the P22 VLP. Dec-facilitated ligand presentation uses genetic fusion of a target protein to the C-terminus of Dec. A poly-histidine tag is maintained on the N-terminus of Dec for purification. Heterologous expression and purification results in a soluble trimeric Dec fusion. The Dec construct can then be used to decorate an EX-P22 sample by mixing the two components (see right-most image). Images were generated using PDB entries 1ALY and 2XYZ.

The Decoration presentation system of the present invention allows for the display of trimeric proteins in a highly polyvalent nanoparticle format while retaining the native structure of the protein.

In one embodiment, the invention provides a fusion protein which comprises, consists essentially of, or consists of an antigen binding domain and a bacteriophage decoration (Dec) protein. When the inventive fusion protein consists essentially of an antigen binding domain and a Dec protein, additional components can be included that do not materially affect the fusion protein. When the fusion protein consists of an antigen binding domain and a Dec protein the fusion protein does not comprise any additional components. Dec proteins are accessory coat proteins that can serve as structural reinforcement for the viral capsid architecture. Dec proteins are common in double-stranded DNA bacteriophages and are readily identified by those of ordinary skill in the art. Examples of Dec proteins known in the art include Soc protein from bacteriophage T4, gpD in bacteriophage lambda, GP8.5 in Φ29 phage, and Dec in bacteriophage L (see, Lander et al., *Structure* 16: (2008), Xiang et al., *PNAS* 108: (2011), Qin et al., *Journal of Molecular Biology* 395 (2010), and Tang et al., *Structure* 14: (2006)). Any Dec protein known in the art, including a fragment of a Dec protein can be used in the inventive fusion protein, so long as the Dec protein can form a trimer and can bind to a virus-like particle (VLP). In one embodiment the Dec protein is from bacteriophage L. In preferred embodiments, the Dec protein comprises the amino acid sequence of SEQ ID NO: 29 or SEQ ID NO: 30.

As used herein, the term "antigen binding domain" is synonymous with target protein and refers to any protein or region of a protein that is known to interact with another protein. In one embodiment of the invention, the antigen binding domain of the fusion protein is a protein of the Tumor Necrosis Factor Super Family (TNFSF). In another embodiment, the antigen binding domain of the fusion protein is the antigen binding portion of a protein of the TNFSF.

The TNFSF, of which CD40L is a member, consists of approximately 20 identified signaling proteins with various roles in cell proliferation, maturation and death particularly within immune processes. The majority of TNFSF members exist as trimeric type II membrane proteins with an extracellular signaling domain, which assumes a conserved triangular pyramid-like structure. Examples of TNFSF include, but are not limited to, TNF-α, VEGI, 4-1BBL (TNFSF9), CD27L (CD70), GIRTL, TRAIL, APRIL, BAFF, FASL, EDA, TWEAK, Lymphotoxin beta, Lymphotoxin alpha, LIGHT, CD30L, RANKL, OX40L, and CD40L. The TNFSF protein or antigen binding domain thereof can be isolated from any species known in the art. In certain embodiments, the TNFSF protein or antigen binding fragment thereof is human or murine TRAIL, CD70, 4-1BBL, GITRL, or CD40L. In a preferred embodiment the TNFSF protein or antigen binding domain thereof of the inventive fusion protein is human or murine CD40L.

In one embodiment of the inventive fusion protein, the Dec protein and the antigen binding domain are connected by a linker region. The linker region can comprise anywhere from 1 to 100 amino acids (e.g., 5, 10, 15, 20, 25, 30, 35, 40, 45, 50, 55, 60, 65, 70, 75, 80, 85, 90, 95 amino acids, or any ranges encompassing these values). The linker region may comprise any amino acid known in the art, such as serine and glycine residues. In a particular embodiment, the linker comprises the amino acid sequence of SGSGSSGS (SEQ ID NO: 1).

The components of the fusion protein can be joined in any particular order. Preferably, the C-terminus of the Dec protein is linked to the N-terminus of the antigen binding domain.

In one embodiment, the fusion protein comprises Dec protein and CD40L. The CD40L or a homologue of CD40L can be isolated from any species, preferably mammalian species such as mouse or human CD40L. The Dec protein and CD40L can be joined by a linker as described herein. In a preferred embodiment the CD40L is human CD40L and comprises the amino acid sequence of SEQ ID NO: 13.

CD40L (CD154), a transmembrane signaling cytokine with a conserved TNF-like trimeric structure, is a key signal in adaptive immunity with applications as an adjuvant in infectious pathogens and cancer immunotherapy.

In another embodiment, the fusion protein comprises Dec protein and TRAIL. TRAIL or a homologue of TRAIL can be isolated from any species, preferably mammalian species such as mouse or human. The Dec protein and TRAIL can be joined by a linker as described herein. In a preferred embodiment TRAIL is human TRAIL and comprises the amino acid sequence of SEQ ID NO: 14 or SEQ ID NO: 15.

TRAIL, a transmembrane signaling cytokine with a conserved TNF-like trimeric structure, binds to certain death receptors causing cell apoptosis and has applications as an adjuvant and in the treatment of cancer.

In another embodiment, the fusion protein comprises Dec protein and CD70. CD70 or a homologue of CD70 can be isolated from any species, preferably mammalian species such as mouse or human. The Dec protein and CD70 can be joined by a linker as described herein. In a preferred embodiment CD70 is mouse CD70 and comprises the amino acid sequence of SEQ ID NO: 16.

CD70 (CD27L) is a transmembrane signaling cytokine with a conserved TNF-like trimeric structure that has applications as an adjuvant and in the treatment of cancer.

In another embodiment, the fusion protein comprises Dec protein and 4-1BBL. 4-1BBL or a homologue of 4-1BBL can be isolated from any species, preferably mammalian species such as mouse or human. The Dec protein and 4-1BBL can be joined by a linker as described herein. In a preferred embodiment 4-1BBL is mouse 4-1BBL and comprises the amino acid sequence of SEQ ID NO: 17.

4-1BBL is a transmembrane signaling cytokine with a conserved TNF-like trimeric structure expressed on activated T lymphocytes, and has applications as an adjuvant and in the treatment of cancer.

In another embodiment, the fusion protein comprises Dec protein and GITRL. GITRL or a homologue of GITRL can be isolated from any species, preferably mammalian species such as mouse or human. The Dec protein and GITRL can be joined by a linker as described herein. In a preferred embodiment GITRL is mouse GITRL and comprises the amino acid sequence of SEQ ID NO: 18.

GITRL (TNFSF18) is a transmembrane signaling cytokine with a conserved TNF-like trimeric structure, and has applications as an adjuvant and in the treatment of cancer.

In one embodiment of the invention the fusion protein comprises the amino acid sequence of SEQ ID NO: 2 (DechCD40L), SEQ ID NO: 19 (DechTRAIL), SEQ ID NO: 21 (DecmCD70), SEQ ID NO: 23 (Decm4-1BBL), SEQ ID NO: 25 (DecmGITRL), or SEQ ID NO: 27 (DechTRAIL-T).

In another embodiment, the fusion protein further comprises a tag. The tag can be any amino acid sequence known in the art that aids in purification (e.g., Flag and polyhistidine), visualization (e.g., GFP and YFP), or localization (e.g. nuclear localization sequence). In a preferred embodiment of the invention the tag is a polyhistidine tag.

The tag of the fusion protein can joined to the fusion protein at any location. For example, the tag may be linked to the N-terminus or C-terminus of the Dec protein or the N-terminus or C-terminus of the target protein. In a preferred embodiment, the tag is located at the N-terminus of the Dec protein. In certain embodiments the tag is directly linked to the Dec protein or target protein (i.e., no additional amino acids between the tag and protein). In other embodiments, the tag is linked to the Dec protein or target protein via any linker region described herein.

The invention also provides a polynucleotide encoding the fusion protein. In one embodiment of the invention the polynucleotide encoding the fusion protein comprises the nucleotide sequence of SEQ ID NO: 3, SEQ ID NO: 20, SEQ ID NO: 22, SEQ ID NO: 24, SEQ ID NO: 26, or SEQ ID NO: 28.

The invention also provides a vector (e.g., recombinant vector) comprising the polynucleotide. Any vector can be used including, but not limited to, plasmids and viral vectors (e.g., adenovirus, adeno-associated virus, retrovirus, and poxvirus). The vector can include regulatory sequences, such as a promoter that optionally is operably linked to the polynucleotide and/or an enhancer.

The invention also provides a composition comprising the fusion protein and a virus-like particle (VLP).

VLPs are non-infectious nano-cage architectures derived from viral sources or other naturally occurring protein cage architectures. These cages can be isolated from infectious viruses by removing nucleic acid cargo or, in some cases, expressed heterologously. VLPs have been shown to act as effective scaffolds for nano-engineering applications including imaging, catalysis, materials construction, cellular targeting and vaccinology. All aspects of a VLP structure are genetically coded and engineering efforts can take advantage of their inherent self-assembly and genetic programmability by utilizing existing VLP proteins to direct protein cargo to different interfaces of the capsid.

The VLP of the inventive composition can be any VLP in which a Dec protein binds and can be isolated from any species in the art. A person of ordinary skill in the art can readily identify VLPs in which a Dec protein binds using methods known in the art. Examples of VLPs for use in the inventive composition include phage lambda, phage T4, P22, and Φ phage. In a preferred embodiment of the invention the VLP is the P22 VLP from *Salmonella typhimurium*.

The P22 VLP adopts an approximately 60 nm T=7 icosahedral structure assembled from 420 copies of the 46 kDa coat protein and as many as 300 copies of the 34 kDa scaffolding protein. The VLPs spontaneously assemble in vivo after heterologous co-expression of these two proteins. Guest proteins can be directed for encapsulation by genetic fusion to the scaffold protein. Initially the VLP adopts a spherical procapsid (PC) morphology but upon heating to 65° C. undergoes a structural transformation to an expanded form (EX), which closely resembles the expansion of the infectious virus during DNA packaging.

In one embodiment of the invention, the VLP encapsulates a guest protein. As used herein, "guest protein" is used synonymously with antigenic protein, and may be any protein known in the art to induce a biological effect (e.g., immune response). In a preferred embodiment of the invention the guest protein is an antigenic protein that can be used in vaccines (e.g., antigenic influenza protein).

The guest protein (e.g., antigenic protein) can be encapsulated within the VLP using any method known in the art. In preferred embodiments the guest protein encapsulation is scaffold protein-directed or via synthetic bioconjugation.

The composition optionally can further comprise, consist essentially of, or consist of a pharmaceutically acceptable (e.g. physiologically acceptable) carrier. When the composition consists essentially of of the inventive fusion protein, VLP, and a pharmaceutically acceptable carrier, additional components can be included that do not materially affect the composition (e.g., buffers, stabilizers, anti-inflammatory agents, solubilizers, preservatives, etc.). When the composition consists of the fusion protein, VLP, and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the fusion protein and VLP described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21*st Edition*, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the inventive composition is administered in a composition formulated to protect the inventive fusion protein and VLP from damage prior to administration. For example, the composition can be formulated to reduce loss of the fusion protein and/or VLP on devices used to prepare, store, or administer the composition, such as glassware, syringes, or needles. The composition can be formulated to decrease the light sensitivity and/or temperature sensitivity of the fusion protein and/or VLP. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the composition, facilitate administration, and increase the efficiency of the inventive method. Alternatively, the composition can be administered in the form of a nucleic acid encoding the fusion protein or a vector comprising a nucleic acid encoding the fusion protein.

TNFSF proteins are known in the art to enhance the immune response and be effective cancer immunotherapeutic agents. Therefore, the invention further provides a method of treating a cancer in a mammal comprising administering a therapeutically effective amount of the composition to the mammal (e.g., mouse, rat, guinea pig, rabbit, cat, dog, goat, horse, cow, primate, human). In a preferred embodiment the mammal is a human).

Cancers that can be treated by the inventive method include, but are not limited to, cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., Eds., pp. 491 762 (15th ed. 2001).

As used herein "treatment," "treating," "treat," "treated," and the like refer to obtaining a desired pharmacologic and/or physiological effect. Preferably, the effect is therapeutic, i.e., the effect partially or completely cures a disease and/or an adverse symptom attributable to the disease.

A "therapeutically effective amount" refers to an amount effective, at dosages and for periods of time necessary, to achieve a desired therapeutic result. The therapeutically effective amount may vary according to factors such as the degree of allergen sensitivity, age, sex, and weight of the individual, and the ability of the composition to elicit a desired response in the individual.

Any route of administration can be used to deliver the composition to the mammal. Indeed, although more than one route can be used to administer the composition, a particular route can provide a more immediate and more effective reaction than another route. Preferably, the composition is administered via intravenous injection. A dose of composition also can be applied or instilled into body cavities, absorbed through the skin (e.g., via a transdermal patch), inhaled, ingested, topically applied to tissue, or administered parenterally via, for instance, intravenous, intraperitoneal, intraoral, intradermal, subcutaneous, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the composition. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The inventive fusion protein and composition can further be used as an adjuvant for vaccinating against a disease or disorder. Thus, the invention further comprises a method of vaccinating against a disease or disorder (e.g., a viral infection such as influenza) comprising administering the composition in which an antigenic protein is encapsulated in the VLP to a mammal (e.g., human). The antigenic protein is not particularly limited, such that the antigenic protein can be any antigenic protein known in the art to induce an immune response against a specific disease. In one embodiment the antigenic protein is an antigenic influenza protein.

The following examples further illustrate the invention but, of course, should not be construed as in any way limiting its scope.

EXAMPLE 1

This example demonstrates the creation of a fusion protein comprising a Dec protein and an antigen binding domain.

In order to facilitate the designed presentation of fusion proteins on the surface of the VLP, antigen binding domains were linked to the C-terminus of a Dec protein via genetic fusion (FIG. 1). As a structurally simple case, the small, monomeric Self-peptide was introduced to form the DecSelf construct. To examine the potential for Dec to present large multimeric proteins, the 148 amino acid soluble region of murine CD40L (AA 112-260), was cloned from a mouse thymus cDNA source and fused to the C-terminus of the Dec protein forming a DecmCD40L fusion construct.

To clone the DecSelf and DecmCD40L fusion proteins, the 21 amino acid CD47 mimic Self-peptide was synthesized as a codon-optimized, annealed primer-set with exposed SacI and HindIII sticky ends (Self fwd and Self rev).

Self fwd:

(SEQ ID NO: 4)
5'-CGGCAACTATACCTGCGAAGTGACCGAACTGACCCGCGAAGGCGAAA
CCATTATTGAACTGAAAA-3'

-continued

Self rev:
(SEQ ID NO: 5)
5'-AGCTTTTTCAGTTCAATAATGGTTTCGCCTTCGCGGGTCAGTTCGGT
CACTTCGCAGGTATAGTTGCCGAGCT-3'

The Self-fragment was ligated into the pET Duet DecWT vector. Proper stop codons were introduced via quickchange PCR using Self stop fwd and Self stop rev primers.

Self stop fwd:
(SEQ ID NO: 6)
5'-CGAAACCATTATTGAACTGAAATAAAAGCTTGCGGCCGCA-3'

Self stop rev:
(SEQ ID NO: 7)
5'-TGCGGCCGCAAGCTTTTATTTCAGTTCAATAATGGTTTCG-3'

The soluble region of mCD40L was cloned from a murine thymus and lymph node cDNA library into the DecWT vector using introduced SacI and HindIII restriction sites (DecmCD40L fwd and DecmCD40L rev).

DecCD40L fwd:
(SEQ ID NO: 8)
5'-TATGAGCTCCAAAGAGGTGATGAGGATCCTCAA-3'

DecCD40L rev:
(SEQ ID NO: 9)
5'-TATAAGCTTTCAGAGTTTGAGTAAGCCAAAAGATG-3'

Truncations of the first 11 or first 20 N-terminal residues were carried out using the Q5 Site-Directed Mutagenesis Kit according to the manufacturer's instructions (New England Biolabs, catalog#E0554) using Dec Δ11 fwd, DecΔ20 fwd and pET rev.

Dec Δ11 fwd:
(SEQ ID NO: 10)
5'-CTATACAAAGATGCTGACGGTGTATATGTGTCTGC-3' pET rev:
(SEQ ID NO: 11)
5'-CGGATCCTGGCTGTGGTGATGATG-3'

DecΔ20 fwd:
(SEQ ID NO: 12)
5'-GTGTCTGCGCTTCCGATTAAAGCTATCAAATACG-3'

The DecWT pETDuet plasmid was used as template DNA. All inserts and mutations were confirmed by DNA sequencing (Eurofins MWG Operon, Inc.). All genetic constructs were confirmed by DNA sequencing.

DecSelf, DecmCD40L, DecΔ11, as well as DecWT, were expressed heterologously in *E. coli* and purified via an N-terminal 6× poly histidine tag. All constructs were transformed into either BL21 (DE3) *E. coli* or ClearColi®. *E. coli* strains harboring expression vectors for the Dec constructs were grown on LB medium at 37° C. in the presence of ampicillin or kanamycin to maintain selection for the plasmid. Expression of the genes was induced by addition of isopropyl β-D-thiogalactopyranoside (IPTG) to a final concentration of 0.5 mM once the cells reached mid-log phase (OD600=0.6). Cultures of DecSelf, DecmCD40L and DecΔ11 were cooled to room temperature before induction in order to encourage a higher percentage of soluble product during purification. Cultures were grown for 4 hours after addition of IPTG, then the cells were harvested by centrifugation and cell pellets stored at −20° C. overnight. Using ClearColi® all constructs were expressed as above but overnight growth was extended from 8 to 16 hrs to account for the approximately 40 min doubling time of the ClearColi® strain.

Cell pellets were resuspended in PBS (50 mM sodium phosphate, 100 mM sodium chloride, pH 7.0) with lysozyme, DNAse and RNAse added and incubated at room temperature for 30 minutes. For Dec constructs, 1 protease inhibitor minitablet (Roche) was added per liter of original culture. The cell suspension was lysed by sonication. Cellular components were removed by centrifugation at 12,000 g for 45 min at 4° C. All His-tagged constructs were purified using a 5 mL Roche cOmplete His-tag purification column. Samples were loaded onto the column in PBS at 2 mL/minute and washed with 40 mL of 50 mM phosphate, 100 mM sodium chloride, 20 mM imidazole pH 7.5. Samples were eluted with an 80 mL gradient from 20-125 mM imidazole. Fractions were collected based on $A_{280}$ and the pooled fractions were dialyzed into PBS or HBS overnight. Samples were concentrated by rebinding to His-tag column, washing with 40 mL of 20 mM imidazole and stepwise elution with 250 mM imidazole in either PBS or HBS. Samples were dialyzed as before to remove imidazole. Concentrations of each construct were determined by UV absorption measured at 280 nm under denatured conditions (5M guanidine hydrochloride) using extinction coefficients calculated using Protein Calculator v3.3 (Chris Putnam, Scripps).

Figure 2A:
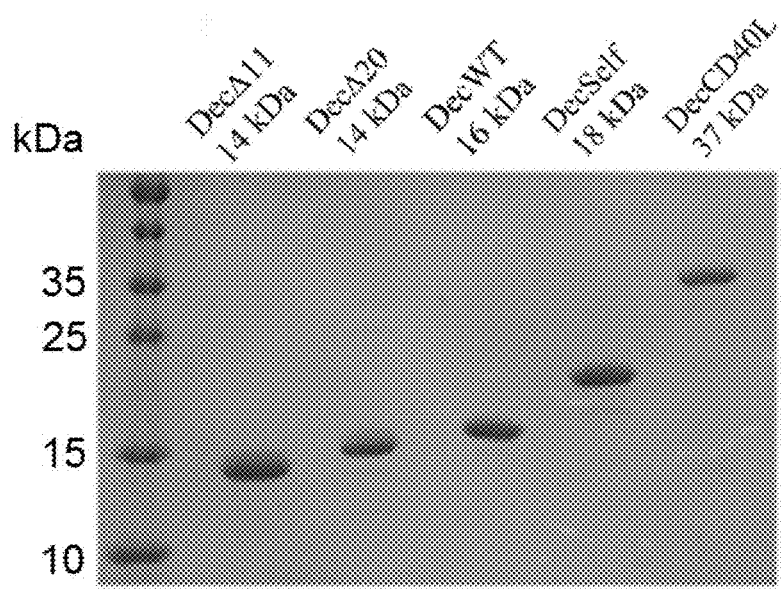
FIGS. 2A-2B demonstrate that the Dec constructs (i.e., fusion proteins) are readily expressed and purified as soluble trimers.

Both chimeric Dec constructs were expressed as soluble proteins although a significant portion of DecmCD40L was observed by SDS-PAGE in the insoluble cell debris following lysis. Lowering the expression temperature to room temperature following induction resulted in higher yields of soluble DecmCD40L. The purity of each construct was assessed by SDS-PAGE. After two passes through nickel-NTA chromatography all samples showed a single band at the expected molecular weight for DecWT (16,175 Da), DecSelf (18,320 Da) and DecmCD40L (36,871 Da) (FIG. 2A). All constructs were stable for at least 3 months at 4° C.

Previous reports have shown that DecWT exists as a trimer in solution. Calibrated analytical size exclusion chromatography (SEC) was performed on a WTC-030S5 (Wyatt Technologies) column on an Agilent 1200 HPLC at 0.7 mL/min of 50 mM phosphate, 100 mM Sodium Chloride and 200 ppm sodium azide pH 7.4. Samples at concentration of ~1 mg/mL were applied in 25 μL injections and detected by absorbance at 280 nm. The void volume was determined using both EX-P22 (MW: 19.6 MDa) and blue dextran (MW: 2 MDa). A calibration curve was established using a Sigma Aldrich Gel Filtration Molecular Weight Markers Kit including equine cytochrome C (12.4 kDa), bovine carbonic anhydrase (29 kDa), bovine serum albumin (66 kDa), yeast alcohol dehydrogenase (150 kDa) and sweet potato β-amylase (220 kDa). Dec samples were run in triplicate and data were fit using IGOR Pro 6.3.

Figure 2B:
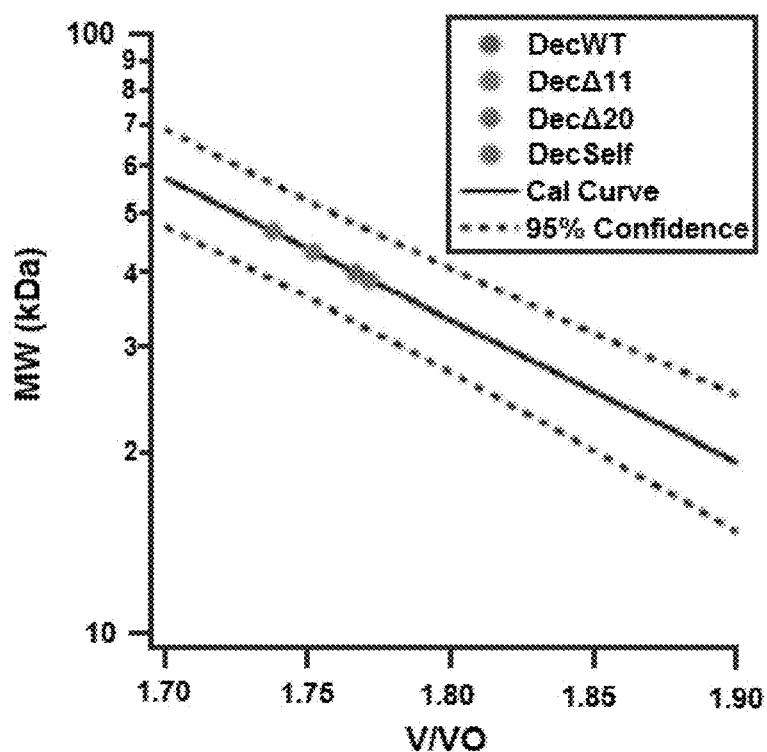

DecWT displayed a single peak at 40±3 kDa, which corresponds well to a trimeric state (43.7 kDa). DecSelf displayed a single peak at 47±3 kDa, which also matches a trimeric state (51.5 kDa) (FIG. 2B). DecSelf was re-analyzed after storage at 4° C. for 4 weeks and exhibited higher molecular weight peaks. To examine the contribution of a cysteine residue in Self-peptide to these higher molecular weight species, the same analysis was performed in the presence of 33 mM DTT. The addition of reductant resulted in the complete disappearance of the higher molecular weight peaks, which shifted to the trimeric peak.

Taken together these data show that the inventive fusion proteins can be solubly expressed and purified, and suggest that Dec can maintain a trimeric structure in the presence of C-terminal fusion.

EXAMPLE 2

This example demonstrates the binding of the fusion protein to a VLP.

An initial assessment of in-solution binding of Dec constructs to the EX P22 VLP was made using size-exclusion chromatography (SEC) coupled with multi-angle and quasi-elastic light scattering (MALS and QELS) respectively. Samples were separated over a WTC-20055 (Wyatt Technologies) size exclusion column and an Agilent 1200 HPLC at 0.7 mL/min of 50 mM phosphate, 100 mM sodium chloride and 200 ppm sodium azide pH 7.4. All capsid samples, with the exception of DecCD40L, bound with Dec constructs were incubated for 30 minutes in 3× stoichiometric excess of the respective Dec construct prior to injection. DecCD40L bound P22 was incubated with 0.8 equivalents of DecCD40L per capsid site due to interactions of the DecCD40L with the column that prevented higher loading in this technique. Total run time was 30 minutes with injection of 25 µL per run. Resultant peaks were detected using a UV-Vis detector (Agilent), a Wyatt HELEOS Multi Angle Laser Light Scattering (MALS) and detector, and an Optilab rEX differential refractometer (Wyatt Technology Corporation). The number average particle molecular weight, Mn, was calculated across each peak half max with Astra 5.3.14 software (Wyatt Technology Corporation) using a previously calculated do/dc value of 0.185 mL/g.

Figure 3A:
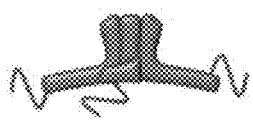
Figure 3B:
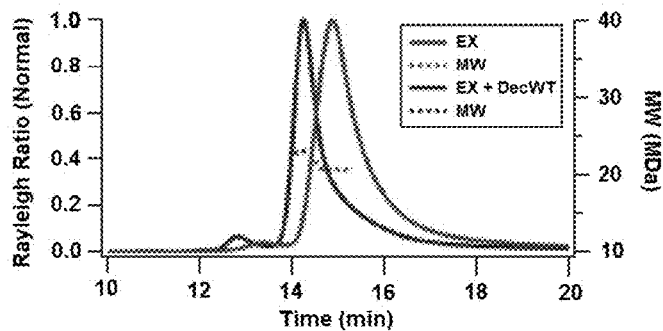

Binding of DecWT to the capsid resulted in a shift in retention time and increase in hydrodynamic radius ($r_h$) of ~1 nm suggesting an increase in the size of the particle. By MALS, the particle mass increased by 2.5±0.2 MDa corresponding to 155±6 DecWT monomers (FIGS. 3A, B, and G). This number suggests partial occupancy with a total expected occupancy of 180 monomers at the 60 quasi-3-fold sites and 60 monomers at the 20 true-3-fold sites for a total possible site occupancy of 240 Dec monomers.

Figure 3C:
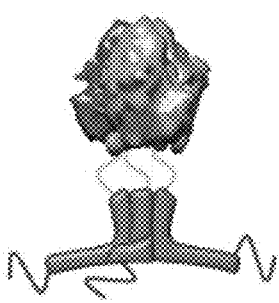
Figure 3D:
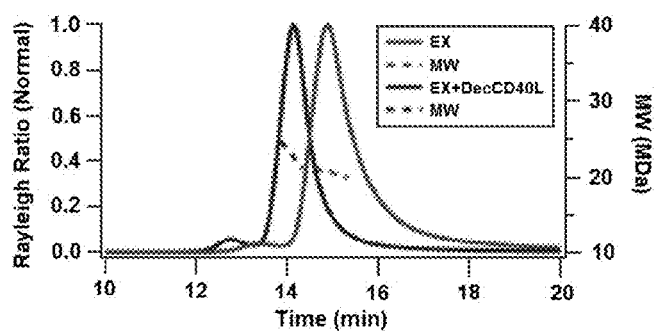
Figure 3E:
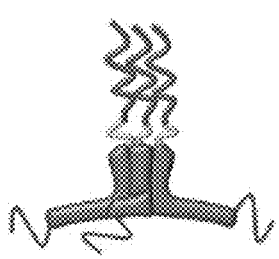
Figure 3F:
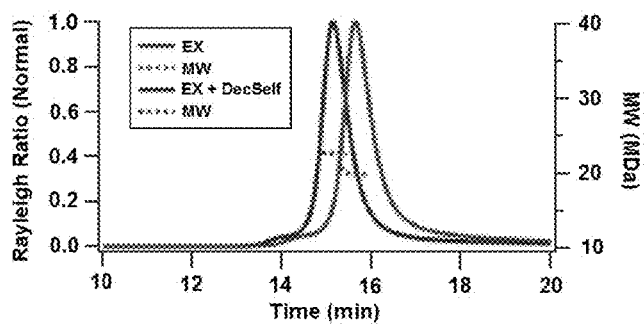

To assess the effect of either CD40L or Self-peptide fusion on Dec binding, in-solution binding was assessed in the same manner as DecWT (FIGS. 3C and 3E). By SEC and QELS both constructs showed retention shifts and increases in the $r_h$ of 1.8 and 1.2 nm for DecCD40L and DecSelf respectively. By MALS, increases in particle molecular weight were observed corresponding to the binding of 51±5 DecCD40L and 114±11 DecSelf monomers (FIGS. 3D, 3F, and 3G). The lower occupancy for these constructs may indicate decreased binding or steric hindrance of adjacent sites. In the case of DecCD40L decreased occupancy is more likely due to the lower number of equivalents of DecCD40L that were used with this sample to avoid the interactions with the column that prevented analytical SEC analysis. SPR results discussed later suggest that both DecCD40L and DecSelf occupy approximately the same number of sites as DecWT.

Figure 4A:
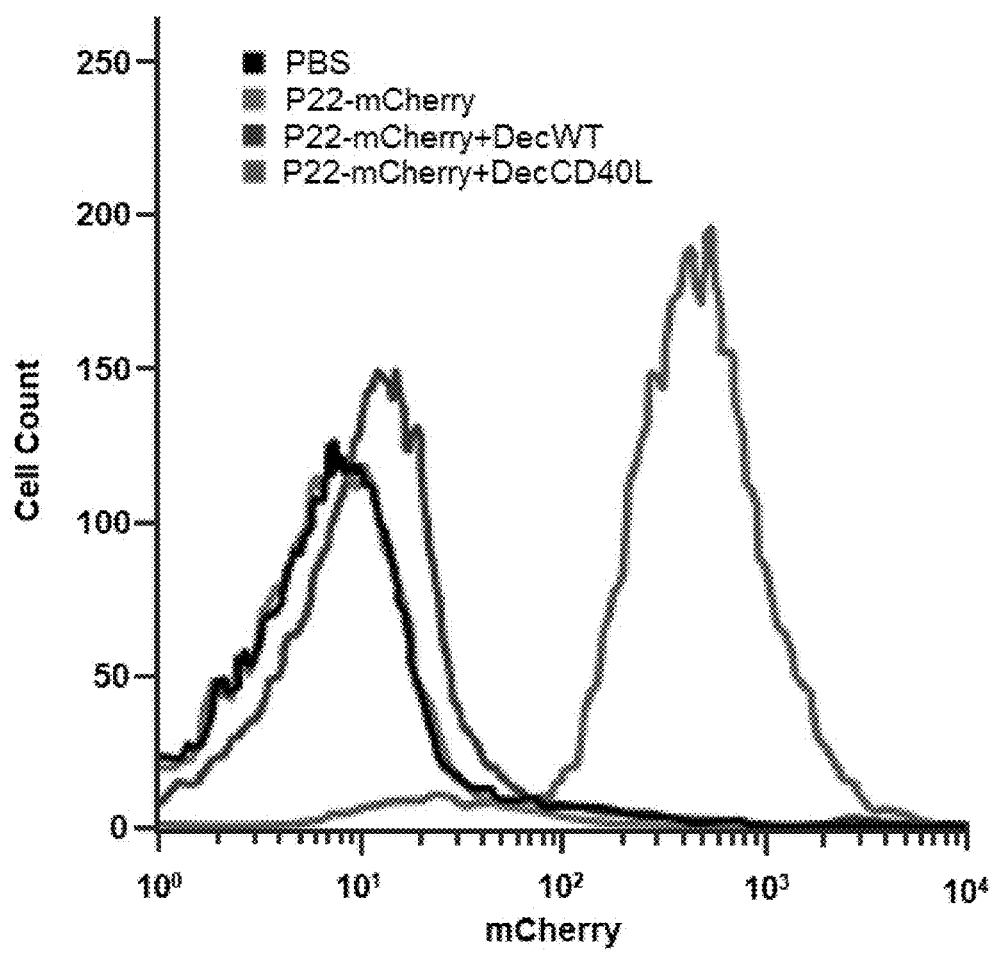
FIGS. 4A-C are graphs of experimental data illustrating VLP bound CD40L fusion proteins maintain binding to CD40.

In addition to maintaining binding to the capsid, target proteins must maintain functionality. To assess the functionality of the CD40L domain, DecCD40L was assayed for binding to primary murine B lymphocytes that display CD40 in high abundance. To avoid phagocytosis of the particles, independent of CD40L-CD40 binding, all incubations were done at 4° C. DecCD40L was bound in excess to EX capsids containing an mCherry-SP fusion protein encapsulated on the interior. CD40L decorated mCherry-P22 incubated with naive murine primary B lymphocytes (B220+, CD19+) showed dramatic increases in binding, assessed by fluorescence-activated cell sorting, compared to P22 alone or P22 functionalized with DecWT, suggesting that the CD40L domain is functional as a fusion to Dec and presented on the surface of P22 (FIG. 4A).

These results show that Dec presentation is largely unaffected by C-terminal fusion. Furthermore, Dec presentation can be used in conjunction with interior encapsulation via genetic fusion to the scaffold protein to create an inside- and outside-functionalized VLP using only genetic means. P22 loaded with mCherry-SP was imbued with affinity for B lymphocytes through decoration with DecCD40L. In addition, uptake of P22 labeled with Cy7 by splenocytes was decreased through decoration with DecSelf thus demonstrating the versatility of the platform.

These results also show that the inventive fusion proteins can bind to the VLP, while maintaining binding to the antigen. Additionally, by delivering the mCherry-SP cargo, this example shows that the inventive composition can result in a spatially controlled bifunctional VLP.

Taken together these data suggest that polyvalent presentation of CD40L trimers, or other TNF family ligands, via the Dec trimer leads to robust signaling and activation by promotion of native quaternary structure and high levels of polyvalent presentation.

EXAMPLE 3

This example demonstrates the fusion protein mediated inhibition of phagocytosis of a VLP.

As discussed above, the Self-peptide is a minimal mimic of CD47, which is a known marker of self and inhibitor of phagocytosis by macrophages. To assess the ability of surface presented DecSelf to decrease particle uptake, decorated VLPs were incubated with primary splenocytes. For ease of detection, P22 particles were labeled internally with Cy7-maleimide. P22-Cy7 alone or P22-Cy7 decorated with DecSelf was incubated with splenocytes at 37° C. to encourage phagocytosis.

Figure 4B:
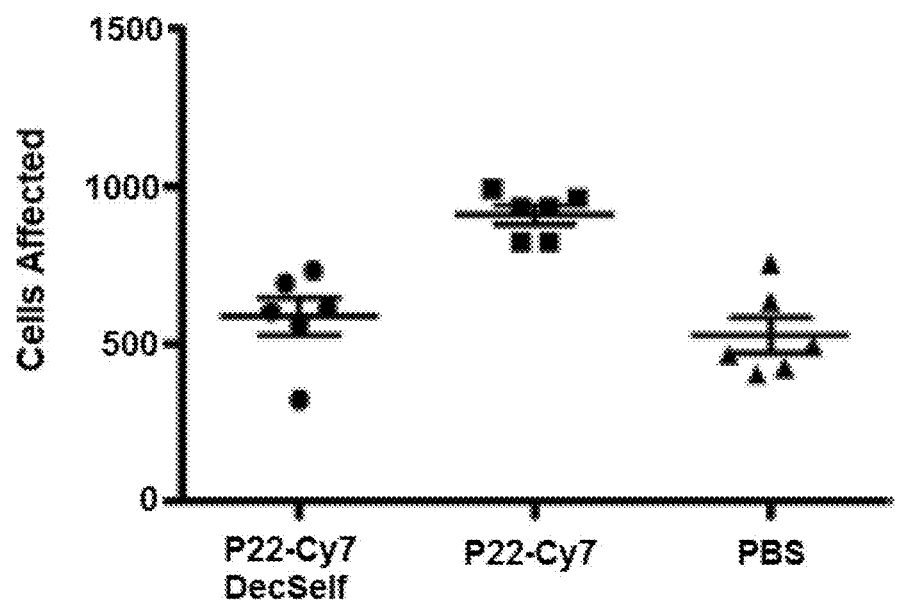
Figure 4C:
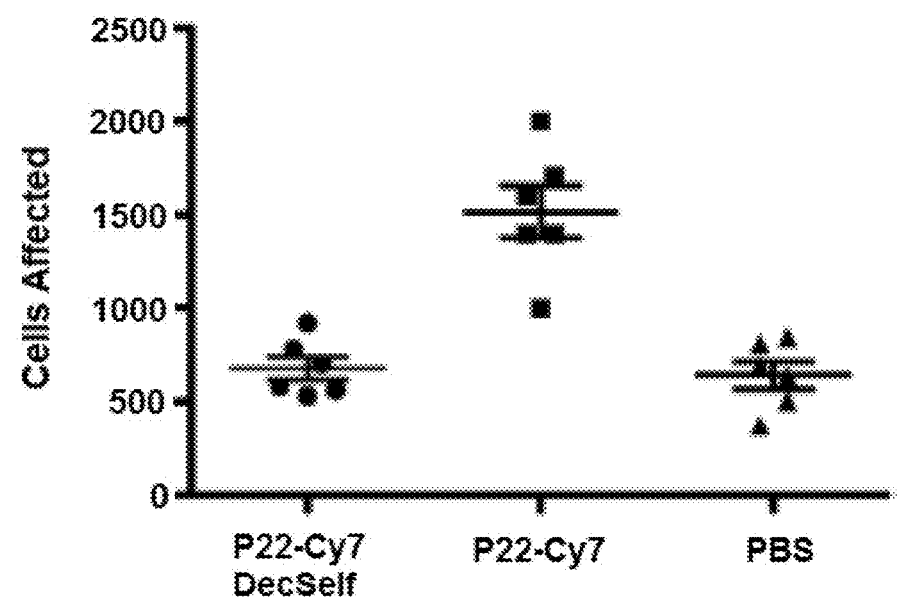

Compared to P22-Cy7, DecSelf associated with cells with lower frequency (P=0.0006) (FIG. 4B). DecSelf association was indistinguishable from PBS controls suggesting minimal interaction. Binding experiments were also performed at 4° C. to assess particle association with the cell surface without uptake. Low temperature trends reflected the same patterns seen at 37° C. (FIG. 4C).

These results suggest that Self-peptide presented as a Dec fusion on the exterior of the VLP remains functional (i.e., binds to SIRP-α and inhibits phagocytosis by macrophages in the same manner as CD47), interrupting association and uptake of particles. These results also suggest that presentation of Self-peptide on the capsid surface may extend capsid circulation time within the body.

EXAMPLE 4

This example demonstrates the kinetics of the fusion protein VLP interaction.

In order for the Dec presentation strategy to be useful in vivo, binding must be stable for hours to days. Previously, fluorescence anisotropy and a single site equilibrium-binding model were used to estimate a $K_D$ of 40-180 nM for Dec with an N-terminal his-tag. It was anticipated that by monitoring the kinetics of binding, the contributions of the two binding sites could be distinguished, the stability of the interaction could be assessed, and the impact of engineering the Dec protein could be better understood.

To monitor binding kinetics a SPR assay was developed. A carboxymethyl dextran surface was functionalized with EX P22 through NHS/EDC coupling. Immobilization levels were estimated to allow for an approximate $R_{max}$ of 250 RU during DecWT binding according to Eq. 1 where S is the number of binding sites per ligand.

EX P22 ligand was dialyzed into 20 mM formate pH 4.4 and diluted to $$R_{Ligand} = \left(\frac{MW_{Ligand}}{MW_{Analyte}}\right) \times R_{Max} \times (1/S) \qquad \text{Equation 1}$$

concentration of 10 μg/mL before being immobilized to a response level of 2,000-2,500 RU. For PC controls, PC P22 was immobilized to ~4,000 RU to account for increased mass and anticipated lack of binding. Previously reported binding parameters and preliminary assays were used to establish a relevant range of analyte dilutions from 0.316-1580 nM for DecWT. For extended dissociation runs, 10 μM DecWT was injected for 3 minutes and then buffer was run for 4 hours before the chip was regenerated. All protein concentration measurements were taken under denatured conditions with an Agilent 8453 UV-Vis Spectrophotometer. Extinction coefficients were calculated using the Protein Calculator tool v3.4 developed by Chris Putnam at the Scripps Research Institute. All SPR measurements were performed using a Bioptix 404PI 4-channel instrument utilizing in-line reference cells to account for bulk effects and non-specific binding.

All data was fit using a user-defined protocol in IGOR Pro 6.3. Data was fit systematically to ensure reasonable initial guesses as input parameters. First the dissociation data at low analyte concentrations, exhibiting only monophasic behavior, were fit independently to a single-site model providing an initial input for the dissociation rate constant ($k_d$) of the high affinity site Eq 2.

$$R(t; t_0 < t) = R_0 e^{-k_d(t-t_0)} \qquad \text{Equation 2:}$$

Where R is SPR signal, $R_0$ is the initial signal intensity as dissociation begins, $t_0$ is the beginning of the dissociation phase. The single-site $k_d$ estimate was initially held constant then allowed to vary in a fit of both the single site on and off rates for the low analyte concentration data-set Eq 3.

$$R(t) = \begin{cases} \frac{R_{max}[A]}{K_D + [A]}[1 - e^{-(k_a[A]+k_d)}] & 0 \le t \le t_0 \\ R_0 e^{-k_d(t-t_0)} & t_0 \le t \end{cases} \qquad \text{Equation 3}$$

Where $R_{max}$ is the signal at saturation or full site occupancy, $k_a$ is the association rate constant, [A] is the concentration of analyte (Dec) and $K_D$ ($k_d/k_a$) is the dissociation constant. The single-site estimates were then used as inputs for the high affinity site in an additive two-site model fit Eq 4.

The association intensities at $t=t_0$ for each specific site, $R_1(t_0)$ or $R_2(t_0)$, are utilized Equation 4:

$$R(t) = \begin{cases} \frac{R_{max1}[A]}{K_{D1} + [A]}[1 - e^{-(k_{a1}[A]+k_{d1})}] + \frac{R_{max2}[A]}{K_{D2} + [A]}[1 - e^{-(k_{a2}[A]+k_{d2})}] & 0 \le t \le t_0 \\ R_{01} e^{-k_{d1}(t-t_0)} + R_{02} e^{-k_{d2}(t-t_0)} & t_0 < t \end{cases}$$

as $R_{01}$ and $R_{02}$ in the dissociation fit at each iteration of the fit to eliminate discontinuity.

Extended dissociation runs were fit to the dissociation of two-independent sites consisting of a sum of two copies of equation 2. Fitting was offset from the switch from sample to buffer injection by 5 seconds to avoid contributions of residual bulk refractive index shifts.

For all fits, parameters were only restricted to non-negative values unless specifically indicated. All data sets were simultaneously fit globally and in triplicate to account for variance between instrument channels. All error is reported as one standard deviation as estimated by IGOR's global fit utility and reflects the uncertainty of the parameter within that specific fit and accompanying parameters.

Figure 5:
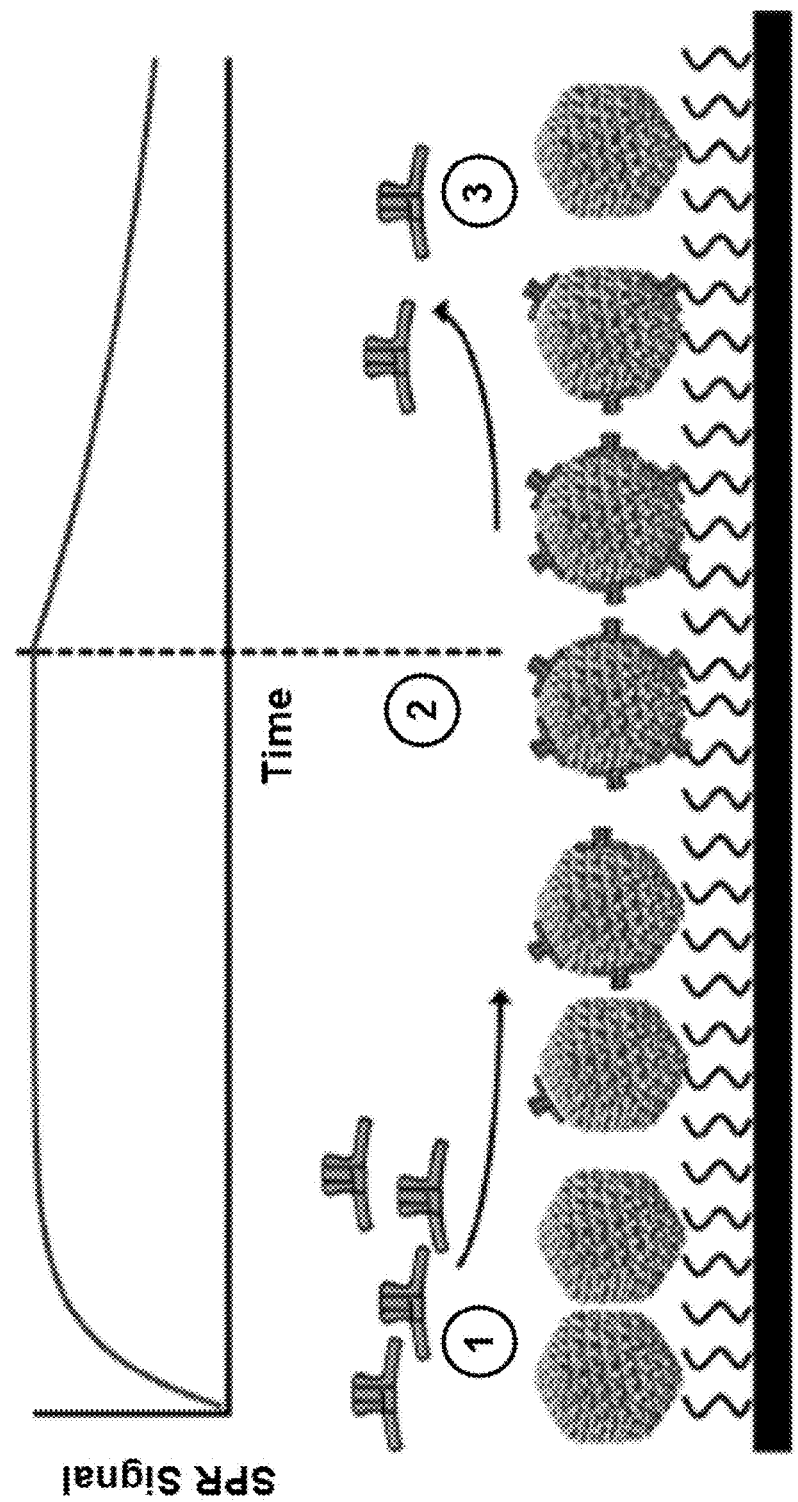
FIG. 5 is a schematic of the SPR kinetic assay. Dec-P22 binding measured by SPR utilizes an NHS/EDC immobilized EX P22 chip. Dec is applied to the chip at a known concentration (1) and binding is monitored by increasing SPR signal. After binding has been allowed to proceed the sample injection is switched to buffer (2). Dec release from P22 is observed by a decaying SPR signal (3). Both the association and dissociation phase are fit simultaneously to a binding model.

EX-P22 was immobilized via NHS/EDC coupling to the chip surface allowing for Dec to be flowed over the surface at known concentrations (FIG. 5). Identification of regeneration conditions that interrupted the Dec-P22 interaction but left the immobilized P22 capsids intact was key to the development of a robust SPR assay. In addition to providing a required method for refreshing the chip surface, regeneration conditions also provided insight into the mechanism of Dec binding to the capsid. Multiple regeneration conditions were screened and pulsed addition of 4 M $MgCl_2$ was shown to completely regenerate the P22 bound surface without interrupting the immobilized capsid integrity. The integrity of the capsid under these conditions was confirmed by SEC. P22 was stable in 4M $MgCl_2$ though Dec was released from the capsid. In contrast, other common regeneration conditions, 0.35 mM EDTA or 20% acetonitrile, did not affect the Dec-P22 interaction. Lower concentrations of $MgCl_2$ were screened as well as a range of LiCl concentrations. High concentrations of LiCl (7 M) resulted in complete regeneration but also caused loss of material from the SPR chip. Short pulses of lower concentrations of either $MgCl_2$ or LiCl resulted in only partial regeneration of the chip surface (data not shown). Disruption of the Dec-P22 interaction with high salt over the short 10 sec pulses utilized here may suggest that the interaction is at least partially electrostatic. However both $MgCl_2$ and LiCl are known to act as chaotropes and thus regeneration could also be the result of partial denaturation of the Dec protein or coat protein.

To assess the kinetics of binding, DecWT was bound to the EX P22 surface at a range of concentrations and both the binding and dissociation were recorded by SPR. Initial binding measurements showed biphasic behavior consistent with two-site binding in the dissociation process at Dec concentrations as low as 100 nM. For this reason, the true affinity of Dec for the high affinity site was anticipated to be higher than reported if the contributions of each site could be deconvoluted.

Accurate data-fitting required that each data-set be fit globally across all concentrations and in triplicate. Common mistakes in global biphasic Langmuir fitting models lie in the numerous models that can describe biphasic behavior. Experimental factors that may cause apparent biphasic signals include heterogeneity of the surface or analyte sample as well as overloading of the ligand surface. These were avoided by extensive purification of Dec samples and the use of an isotropic virus particle as the immobilized ligand. Chip loading with P22 was carefully monitored in real-time and terminated at levels estimated to be below the threshold for mass-transport limitations (Equation 1). This was confirmed by the absence of characteristic linearity in the early association phase. A simple two-independent binding site model was anticipated based on previous reports showing Dec binding to both the 3-fold (low-affinity) and quasi-3-fold (high-affinity) sites of the P22 capsid.

Another factor complicating global fitting in general is the strong dependence on the initial input values. To avoid non-descriptive solutions, the data were fit systematically. First, low concentration data not displaying biphasic shape, at 100 nM Dec and below, were fit to a single-site binding model providing an initial estimate of association rate constants ($k_a$) and dissociation rate constants ($k_d$). Estimates for $k_a$ and $k_d$ were then used as inputs for the first site of a two-site binding model, initially held fixed and then allowed to vary after reasonable inputs had been obtained for the rate constants for the second site ($k_{a2}$ and $k_{d2}$).

Figure 6A:
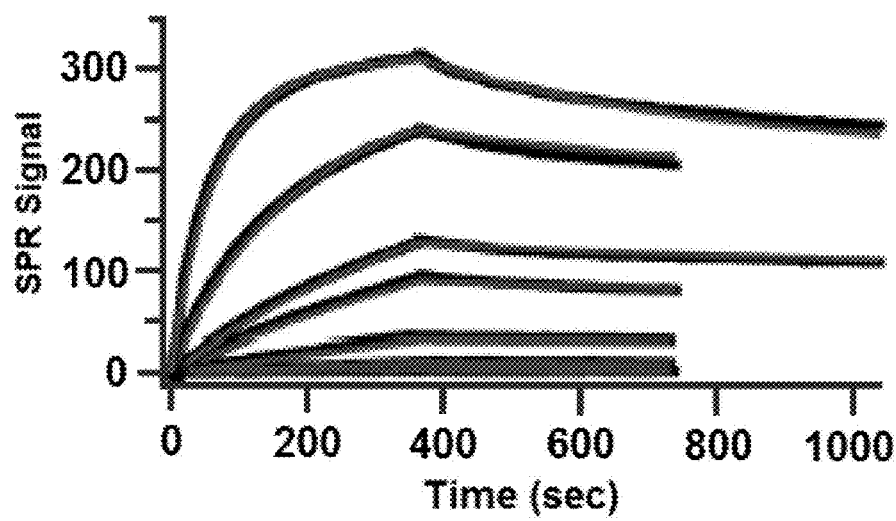

As anticipated, binding of DecWT over the full range of concentrations assayed was poorly fit by a single-site Langmuir model (Equation 3) but matched well with an expected two independent site Langmuir model (Eq. 4, FIG. 6A). While the two sites of the capsid may not be truly independent, previous cryo-EM reconstructions showed no evidence to justify using a more complex allosterically connected two-site model. As expected DecWT was shown to bind with higher than reported affinity to the high-affinity binding site ($k_a$: 11,540±30 $M^{-1}$ $sec^{-1}$, $k_d$: 1.06±0.06×$10^{-4}$ $sec^{-1}$, $K_D$: 9.2±0.5 nM) and with micromolar affinity to a second lower affinity binding site ($k_a$: 1,980±146 $M^{-1}$ $sec^{-1}$, $k_d$: 2.98±0.06×$10^{-3}$ $sec^{-1}$, $K_D$: 1,502±115 nM). Low-concentration single-site fitting results were in agreement with the tighter binding site parameters from the two-site binding fit ($k_a$: 13,832±93 $M^{-1}$ $sec^{-1}$, $k_d$: 3.30±0.03×$10^{-4}$ $sec^{-1}$, $K_D$: 24.0±0.3 nM).

Figure 6B:
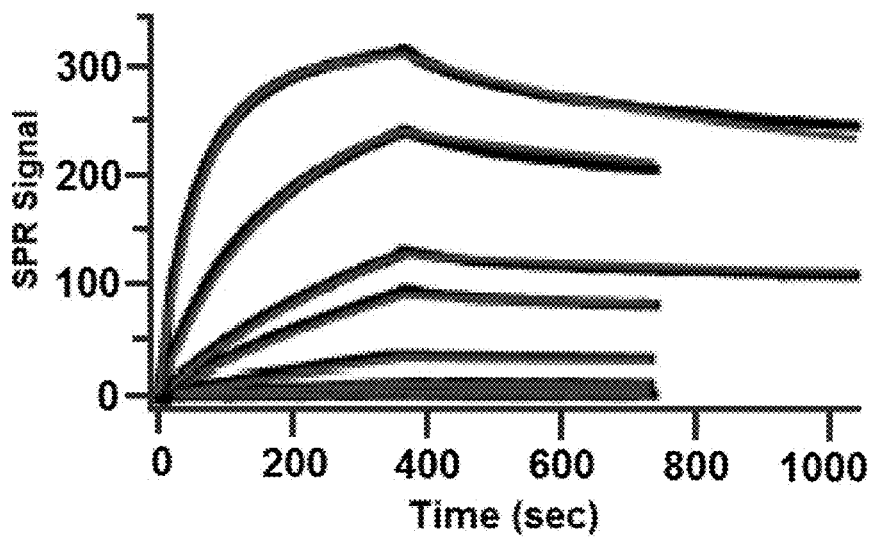

Despite sensitivity to variation in all other parameters, the fit was insensitive to fixing the $k_d$ of the tight-site to lower values. This is not surprising as minimal curvature due to the tight site can be observed in the ten-minute dissociation time of these runs (FIG. 6A). Thus, parameter outputs of this initial fit serve only as maximum estimates for the $k_d$ of this site and may not reflect the actual $k_d$. Significant reduction in the $k_d$ for both sites were observed ($k_{d1}$: 3.20±0.04×$10^{-6}$ $sec^{-1}$, $k_{d2}$: 9.50±0.05×$10^{-4}$ $sec^{-1}$) (FIG. 6B). Despite the extended run time there was still minimal curvature observed for the tight-site suggesting that the $k_d$ may be even lower. In addition, deviation from good fit was observed early in the run where the curvature due to lower affinity interactions is most evident. This disagreement suggests an interaction that is more complex than an independent two-site model possibly due to sterics or allostery. Such an effect could be due to changes in the dynamics of the capsid upon binding such as seen with GpD and bacteriophage lambda.

To assess the highest affinity interaction the $k_d$ of the tight site was fixed in the two-site fit across the full concentration data-set. Minimal deviation was seen in other parameters resulting in a $K_D$ for the tight site of 0.255±0.003 nM (FIG. 6E). These parameters indicate a half-life of Dec binding at the tight-site of at least 60 hrs.

This affinity suggests that the inventive fusion protein has the potential to stay associated with the VLP for extended periods of time highlighting the potential utility of this system for in vivo applications.

Figure 6C:
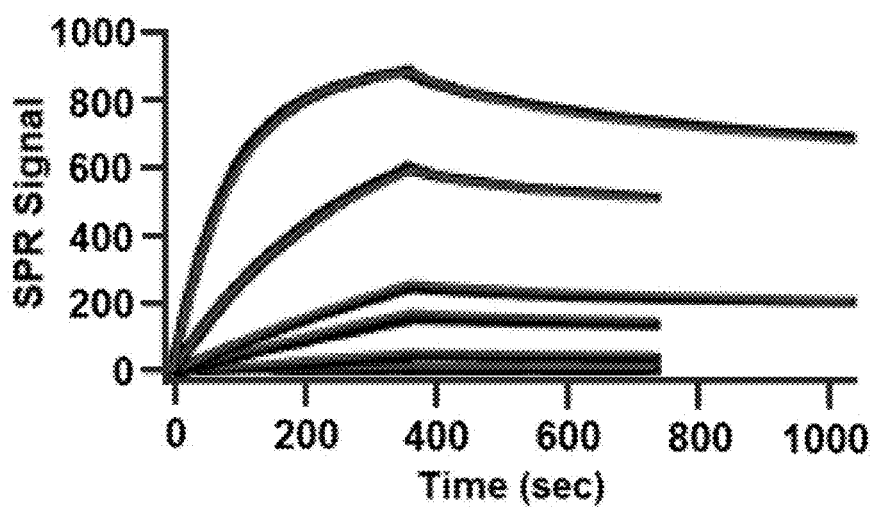

Binding kinetics were measured for DecCD40L and DecSelf using the same immobilized P22 chip surface as for the DecWT experiments. Both constructs showed increased equilibrium signal at the same concentrations compared to DecWT indicating a larger mass deposition on the chip surface. Assuming that the same number of surface sites (P22) were available and being occupied, these results suggest that, as expected, the analyte had a larger molecular weight than DecWT. The binding of Dec constructs was compared to DecWT two-site fit without fixing the tight-site $k_d$. Kinetic fitting of the DecCD40L showed minimal change in affinity at the tighter binding site ($k_a$: 6,439±4 $M^{-1}$ $sec^{-1}$, $k_d$: 2.0±0.03×$10^{-4}$ $sec^{-1}$, $K_D$: 30.8±0.4 nM) and maintenance of the weaker binding site affinity despite the presence of the fused CD40L domain (FIGS. 6C and 6E). As with DecWT, fitting of the low concentration data-set for DecCD40L by a single site model resulted in agreement with the tighter-site parameters of the two-site model.

Figure 6D:
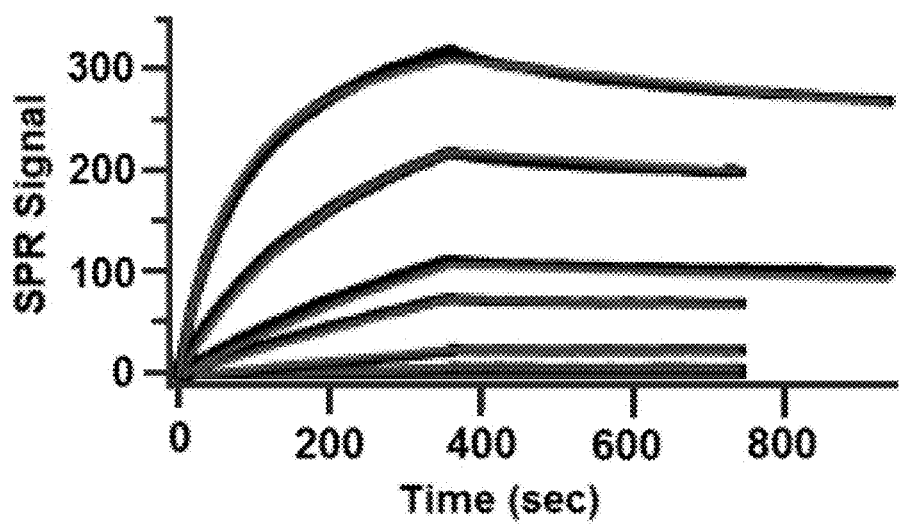

DecSelf also maintained biphasic-binding behavior but the fit to a simple two-site model was not as robust as for DecWT or DecCD40L (FIG. 6D). Nevertheless results for DecSelf binding to the tighter binding site ($k_a$: 11,246±80 $M^{-1}$ $sec^{-1}$, $k_d$: 2.0±0.03×$10^{-4}$ $sec^{-1}$, $K_D$: 18.3±0.3 nM) showed minimal change from DecWT (FIG. 6E). Fit disagreement may be the result of some aggregation of DecSelf due to the cysteine in the Self-peptide as seen in the aged sample described above. DecSelf samples were prepared fresh for the SPR experiment and the uniformity assessed by SEC but any cross-linked species in the population formed subsequently could have contributed to fitting error.

As mentioned above, SEC MALS is not an ideal method for monitoring the relative occupancy of Dec constructs at the available sites of the capsid due to the delay time between the sample being taken out of equilibrium and being monitored. SPR has previously been used to compare the stoichiometry of interactions and an estimate of the relative occupancy was calculated from net $R_{max}$ obtained from the kinetic fit of the SPR data. The net $R_{max}$, the sum of the $R_{max}$ from the tight site and the weak site of the fit, reflects the projected maximum signal due to binding of the Dec construct to the EX-P22 surface. For the same chip surface $R_{max}$ can be compared to give a relative occupancy based on the molecular weight of the construct. For DecCD40L the relative binding compared to DecWT was 2.61±0.06 compared to the expected value of 2.28 based on the ratio of the construct MW. For DecSelf relative binding was calculated to be 0.94±0.04 compared to the expected value of 1.13. Discrepancies between the expected and calculated values could be the result of slight differences in occupancy but are more likely a consequence of slight disagreements in the fitting of the data to a simple two-site model.

The mechanism and kinetics of binding were analyzed providing key insights into further engineering of the Dec system. Surface Plasmon Resonance (SPR) distinguished between the contributions of a tighter and weaker interaction demonstrating sub-nanomolar affinity in the highest affinity interaction, nearly 3 orders of magnitude tighter than previous estimates. The VLP-Dec interactions, localized to the Dec N-terminal region, are likely charge-mediated and the binding interaction can be modulated by ionic strength. Additionally, a Dec-binding particle population within heterologously expressed VLPs was identified that may represent semi-conserved defect particles.

Taken together these results suggest that Dec tolerates large fusions at its C-terminus and, while there may be subtle differences in the binding behavior, largely maintains binding to the capsid. Moreover, the data suggests that the inventive fusion protein has the potential to stay associated with the VLP for extended periods of time highlighting the utility of this system for in vivo applications.

EXAMPLE 5

This example demonstrates the Dec binding regions for the interaction with the VLP.

Figure 7A:
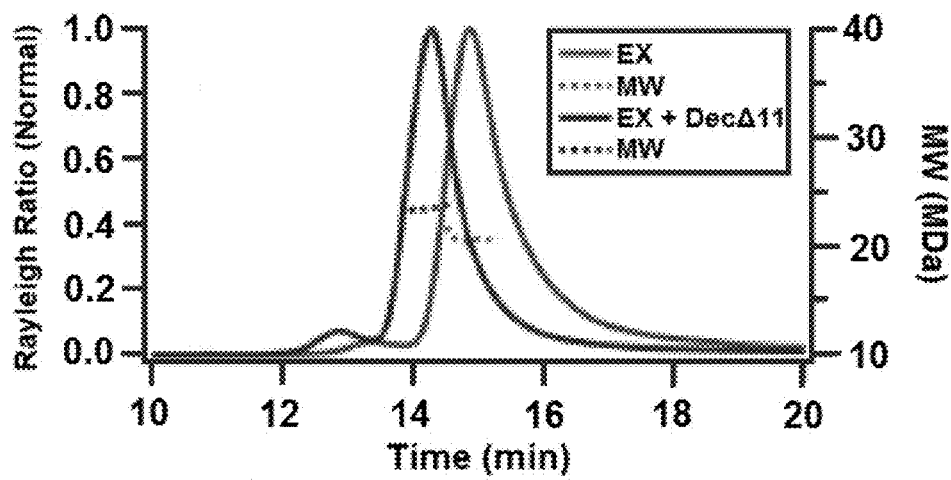
FIGS. 7A-7D are graphs of experimental data illustrating the key Dec binding regions for the VLP. DecΔ20, but not DecΔ11, shows a severe reduction in binding to EX P22.
Figure 7B:
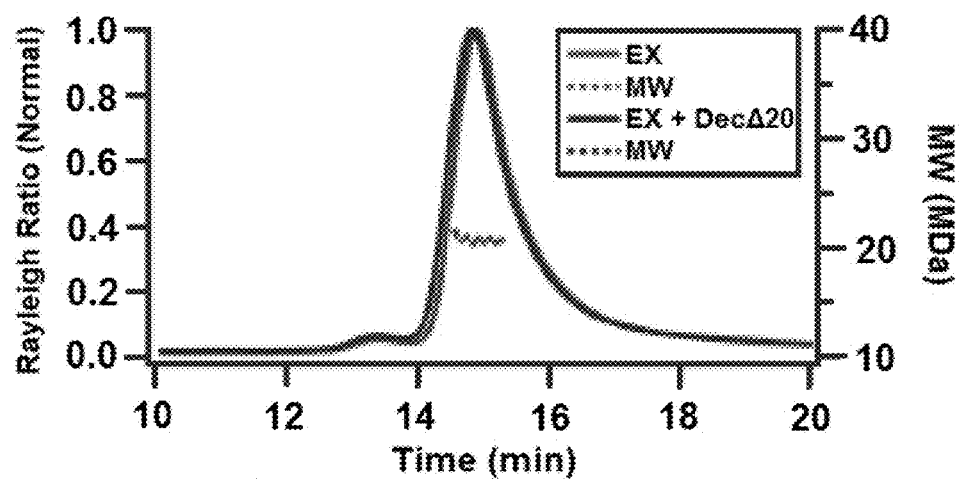

To further examine the mode of Dec binding and in an effort to potentially identify intermediate affinity Dec mutants, truncations of either the first 11 (DecΔ11) or 20 (DecΔ20) N-terminal residues were generated and analyzed for stability and binding. By calibrated SEC, both the DecΔ11 and DecΔ20 showed only single peaks at 43±3 and 39±3 kDa, respectively, which best corresponded to a trimeric structure (43.4 and 40.3 kDa) (FIG. 2B). This suggests that key trimerization residues for the Dec protein are not located in the N-terminal 20 residues. In-solution binding assessed by SEC-MALS-QELS showed that DecΔ11 binding results in increased particle molecular weight and a retention shift but binding of DecΔ20 is completely absent (FIGS. 3G, 7A, and 7B).

Figure 7C:
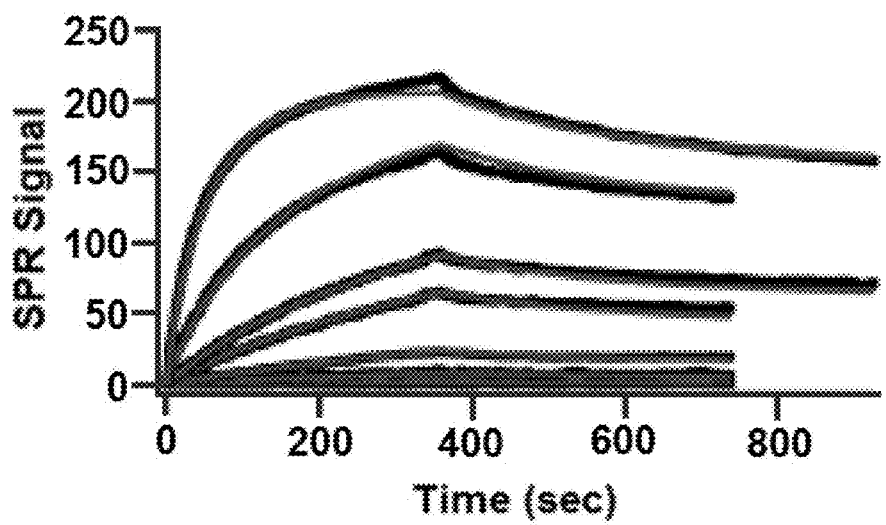
Figure 7D:
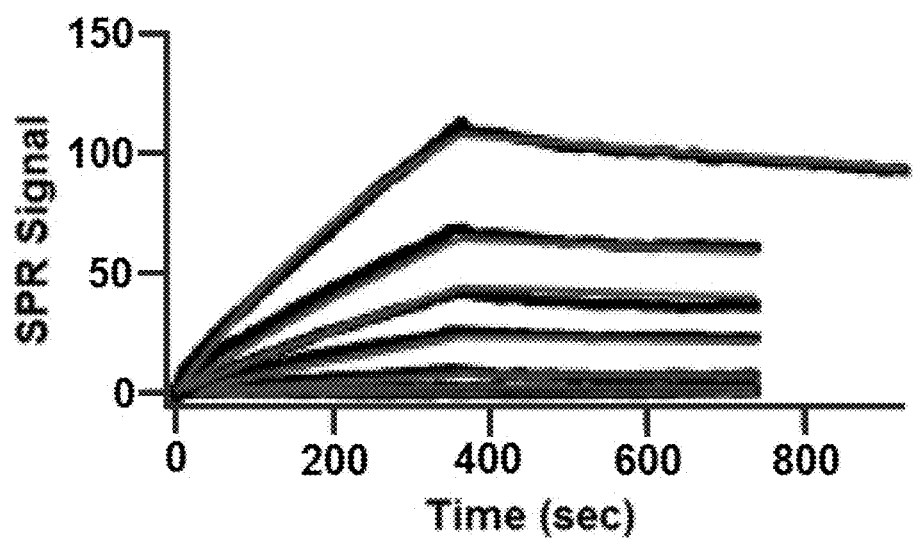

The kinetics of binding for both DecΔ11 and DecΔ20 were assessed by SPR. DecΔ11 bound with similar affinity to DecWT at both the tight and weak binding sites (FIGS. 6E and 7C). DecΔ20 bound with significantly reduced affinity. DecΔ20 binding data did not display biphasic behavior over a concentration range of 0.032-31.6 μM. Fitting to a single-site model showed a more than 300-fold reduction in $K_D$ from the high-affinity site of DecWT (FIGS. 6E and 7C). The estimated relative occupancy for both constructs was assessed using the net $R_{max}$. Both DecΔ11 and DecΔ20 displayed less than expected binding relative to DecWT but, as mentioned above, this may be explained by deviations in the fit as opposed to actual reduced site occupancy. The constructs showed an expected progressive decrease in the net $R_{max}$ with reduced MW.

Amino acid sequences of the N-terminus were compared between DecWT, DecΔ11 and DecΔ20. Notably DecΔ20, but not DecΔ11, loses charged residues compared to DecWT charged residues (K14, D15 & D17). While there may also be contributions from loss of essential structure due to truncation, the loss of binding with the loss of charged sites is consistent with the observed reversibility of the Dec-P22 interactions at high ionic strength.

These results suggest that the N-terminal domain of Dec is responsible for binding to the capsid. Specifically the section from amino acids 11-20 is critical for the binding interaction. Binding of Dec was reversed at high ionic strength suggesting that the interaction is at least partially charge-mediated. This insight can be used to design Dec constructs with alternative binding affinities to the capsid, allowing for control over processes such as Dec-mediated higher order assembly of capsids or release of the Dec-cargo from the capsid under controlled conditions.

EXAMPLE 6

This example demonstrates that disulfide cross-linked Dec-induced aggregation removes a PC-like subpopulation.

Figure 8A:
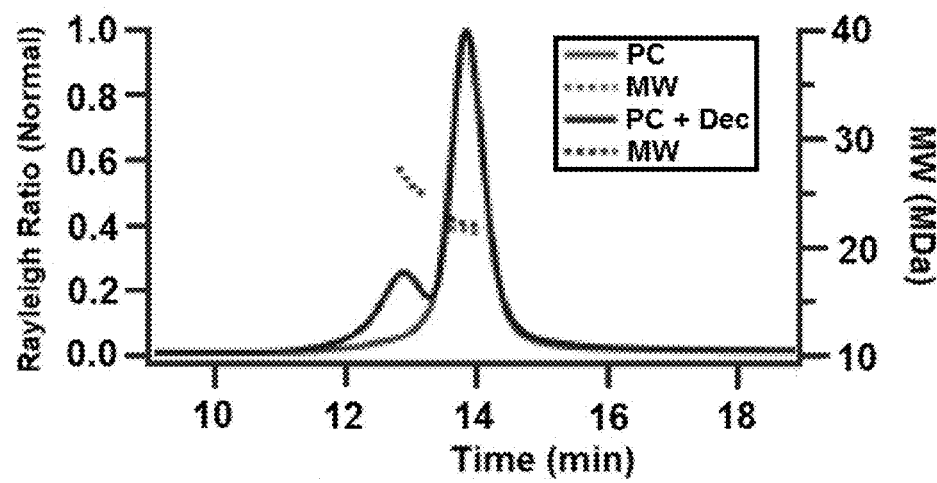
FIGS. 8A-8E depict the results of experiments illustrating that disulfide cross-linked Dec induced aggregation removes a PC-like subpopulation.

In initial examination of the Dec-P22 interaction it was found that a subpopulation of P22-PC binds Dec, in apparent contradiction of reports in the literature where Dec does not bind to the PC morphology (FIG. 8A). This suggested that the sample (purified by ultracentrifugation and SEC) was contaminated with a sub-population that could not be removed via normal purification procedures.

Figure 8B:
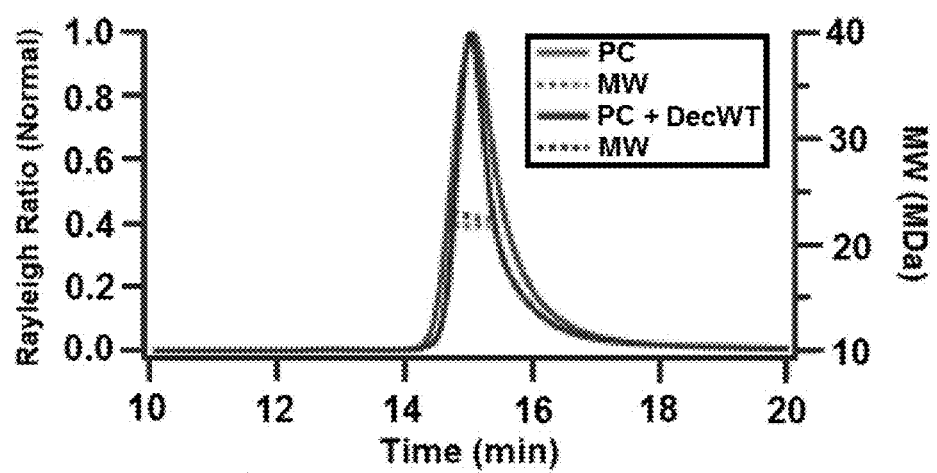
Figure 8C:
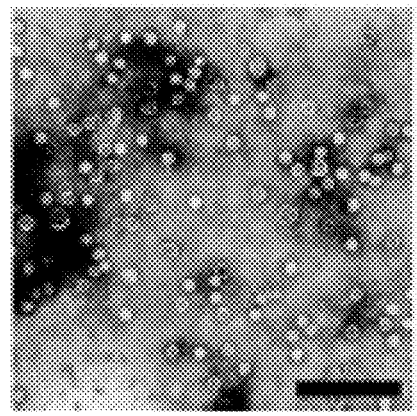
Figure 8D:
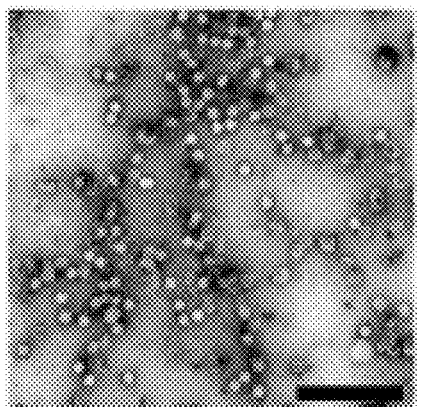
Figure 8E:
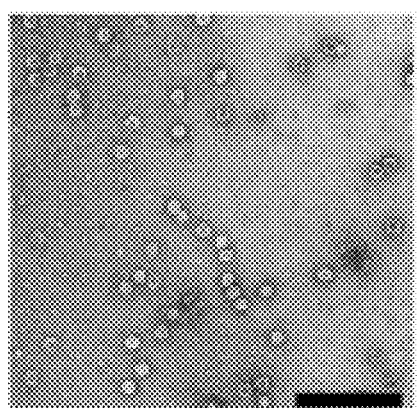
Figure 9:
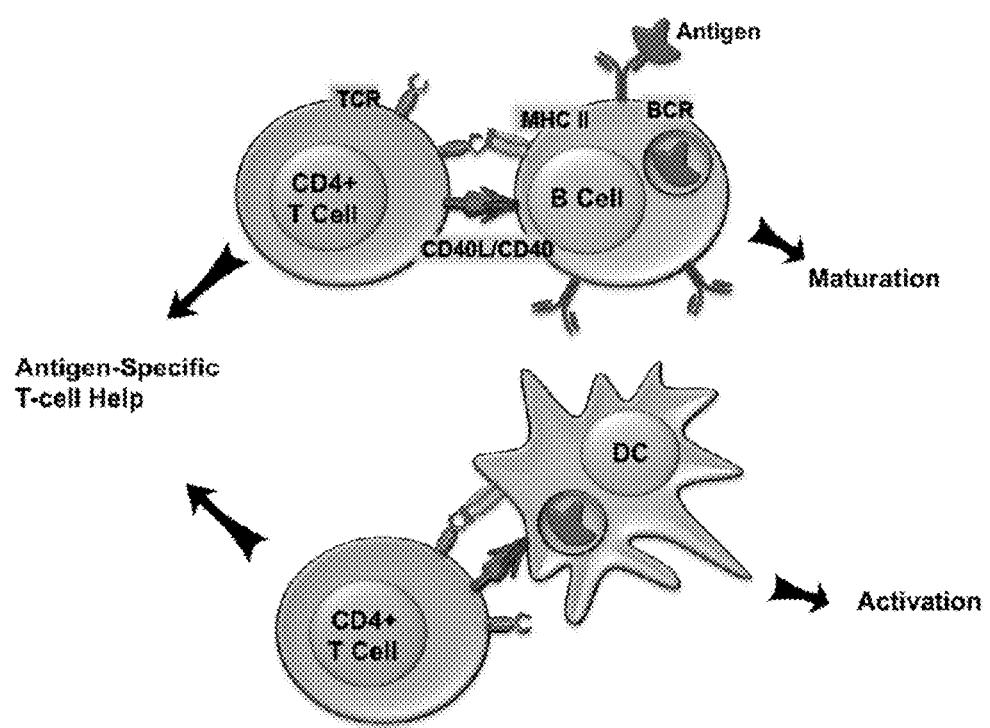
FIG. 9 is a schematic demonstrating that CD40L is a gateway between innate and adaptive immunity. An antigen is uptaken by an antigen-presenting cell (APC) (represented as a B-cell or dendritic cell (DC) here). The antigen is processed and presented via MEW II, which engages a specific CD4+ T cell through the T cell receptor (TCR). The CD40-CD40L interaction stimulates the APC to mature and subsequently stimulate maturation of the T-cell allowing for the initiation of effective adaptive immunity.

To remove the sub-population from the PC sample a C-terminal cysteine mutant of Dec (DecS134C) was used, which upon oxidation forms a linear head-to-head dimer of trimers that can crosslink and aggregate particles to which it binds. The percentage of this sub-population in the P22-PC sample was found to vary from batch to batch and could be purified away through Dec-Dec aggregation. The remaining PC was shown to have no measurable affinity for Dec (FIG. 8B). Aggregated particles were resolubilized with 30 mM DTT and compared to non-aggregated particles by transmission electron microscopy (TEM). Particles in the aggregate showed higher frequency of cracked or incomplete particles compared with the original sample while the remaining particles after aggregation were almost completely devoid of misformed particles (FIG. 8C-8E).

This P22-PC sub-population is indistinguishable by SEC, density-gradient ultracentrifugation and non-denaturing agarose gel electrophoresis. Only TEM reveals the presence of the sub-population, which is evident as mis-formed or incomplete particles. Formation of this sub-population is likely a consequence of an imbalance in the relative production of coat protein and scaffold protein during heterologous expression. Aberrant assemblies of P22 have been reported and can usually be separated by centrifugation or SEC. The sub-population could also be due to a small amount of carry-over from an aberrant P22 peak that precedes the intact particle peak in nearly every heterologously expressed P22 VLP batch. However given the quantity of these particles a more likely explanation is that the particles are imperfect T=7 capsids that co-elute with PC on SEC (FIG. 8A). Interestingly the Dec binds extremely well to the aberrant assemblies and the Dec-Dec dimer precipitation was utilized as an effective method of purification.

EXAMPLE 7

This example demonstrates that fusion protein can be readily expressed. Dec forms a C3 symmetric trimer in the capsid-bound orientation with the C-termini of the monomers clustered and protruding away from the capsid surface. This symmetry matches that of CD40L and the rest of the TNFSF. From crystallographic studies both the C and N termini of CD40L are located adjacent to the cell surface and opposite the active signaling CD40-binding sites and should allow for a strain-free fusion between the N-terminus of CD40L and the C-terminus of Dec.

An N-terminal 6× histidine tag DecWT gene was ligated into a pET Duet vector via BamHI and SacI sites. A gene fragment coding for the soluble region of human CD40L (AA 114-261) and 25 base pair flanking regions matching the target plasmid insertion site was ordered as a gBlock® from Integrated DNA Technologies Inc. DecWT pETDuet was amplified using the Dec_pETDuet fwd and rev primers, which removed the stop codon of the Dec gene.

```
Dec_pETDuet fwd:
                                  (SEQ ID NO: 31)
GAGCTCGGCGCGCCTGCAGGTCGACAAGCTT Dec_pETDuet rev:
                                  (SEQ ID NO: 32)
GGATCCACTTCCTGATGTTGTTTCGATAGTC
```

The DechCD40L plasmid was assembled using NEBuilder® HiFi DNA Assembly Mix as per manufacturer's suggestions. Insertions and mutations were confirmed by DNA sequencing (Eurofins MWG Operon, Inc.).

All constructs were transformed into ClearColi®. Strains harboring expression vectors for the DecCD40L or for the P22 CP and SP were grown on LB medium at 37° C. in the presence of ampicillin to maintain selection for the plasmid. Expression of the genes was induced by addition of isopropyl β-D-thiogalactopyranoside (IPTG) to a final concentration of 0.5 mM once the cells reached mid-log phase (OD600=0.8). Cultures of DechCD40L were briefly cooled on ice at the point of induction and allowed to continue growing at room temperature. Cultures were grown for 4 hours after addition of IPTG, harvested via centrifugation and cell pellets stored at −20° C. overnight.

Cell pellets were resuspended in PBS (50 mM sodium phosphate, 100 mM sodium chloride, pH 7.0) with lysozyme, DNAse and RNAse added and incubated at room temperature for 30 minutes. The cell suspension was lysed by sonication. Cellular components were removed by centrifugation at 12,000 g for 45 min at 4° C. P22: P22 samples were purified from the post-lysis supernatant by ultracentrifugation through a 5 mL 35% (w/v) sucrose cushion. The resulting viral pellet was resuspended in PBS (50 mM sodium phosphate, 100 mM sodium chloride, pH 7.0) and centrifuged at 16,000 g for 20 min to remove any remaining aggregates. Samples were then purified over an S-500 Sephadex (GE Healthcare Life Sciences) size exclusion column using a Biorad Biologic Duoflow FLPC. Fractions containing P22 were concentrated by ultracentrifugation and the resulting viral pellet was resuspended in an adequate volume of PBS or HBS (50 mM HEPES, 100 mM NaCl, pH 7.0). Dec: All his-tagged constructs were purified using a 5 mL Rosche cOmplete his-tag purification column. Samples were loaded onto the column in PBS at 2 mL/minute and washed with 40 mL of 50 mM phosphate, 100 mM sodium chloride, 20 mM imidazole pH 7.5. Samples were eluted with an 80 mL gradient from 20-125 mM imidazole. Fractions were collected based on $A_{280}$ and the pooled fractions were dialyzed into PBS or HBS overnight. Samples were concentrated by rebinding to His-tag column, washing with 40 mL of 20 mM imidazole and stepwise elution with 250 mM imidazole in either PBS or HBS. Samples were dialyzed as before to remove imidazole. Concentrations of each construct were determined by UV absorption measured at 280 nm under denatured conditions (5M guanidine hydrochloride) using extinction coefficients calculated using Protein Calculator v3.3 (Chris Putnam, Scripps).

Procapsid P22 at 2 mg/mL was heated for 25 min in a water bath at 67° C. Expansion was confirmed via nondenaturing 1% agarose gel electrophoresis at 65 volts for 2 hours in TAE buffer (40 mM Tris, 20 mM acetate, 1 mM EDTA pH 8.0) stained with InstantBlue™.

Figure 10A:
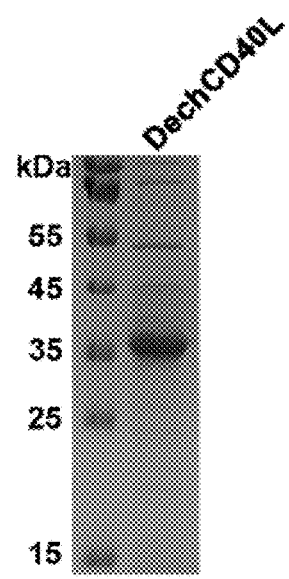
FIGS. 10A-10B are experimental results illustrating that a Dec-human CD40L fusion (i.e., DechCD40L) can be purified as a soluble product and readily binds to the P22 VLP.
Figure 10B:
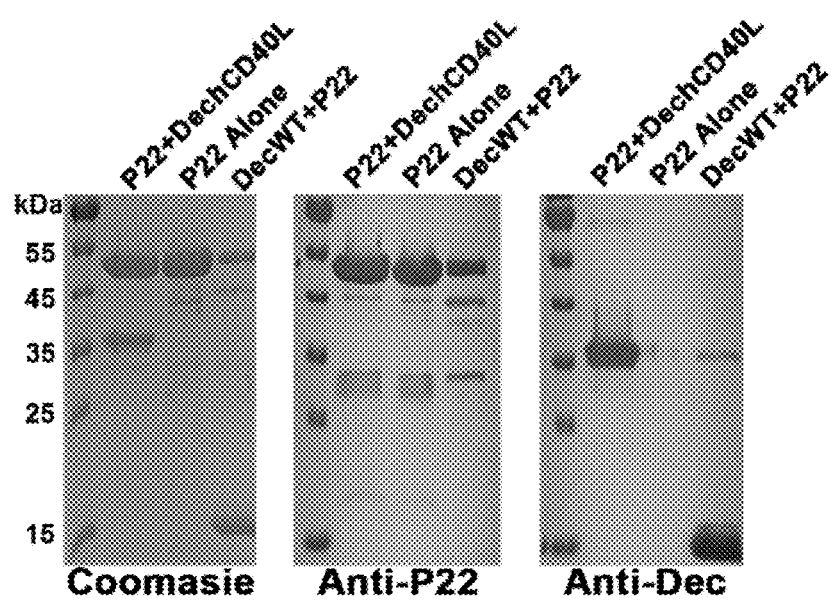

A codon optimized gene coding for the soluble extracellular region of human CD40L was fused to the C-terminus of the Dec gene separated by an eight amino acid linker consisting of flexible glycines and serines to form a continuous DechCD40L gene. Expression of DechCD40L and purification via an N-terminal 6× histidine tag resulted in a band by SDS-Page, which matched well with the expected molecular weight of 32.7 kDa (FIG. 10A). Initial mixture with EX P22 followed by ultracentrifugation demonstrated that DechCD40L binds to the capsid and the identity was further confirmed by western blot analysis using a polyclonal anti-Dec Ab mixture (FIG. 10B).

EXAMPLE 8

This example demonstrates the spatial orientation of the fusion protein on the VLP capsid.

DecmCD40L decorated capsids bind to primary murine B-cells displaying CD40 in high abundance. These results suggested that mCD40L in the presented context was accessible for binding to CD40 on the B-cell surface.

Cryo-EM reconstructions were generated for EX-P22 VLPs with and without DechCD40L bound (FIGS. 11A and 11B). Additional density was present at all expected Dec binding sites, both high affinity and low affinity. Less density was present at the true 3 fold sites, which have been previously identified as lower affinity. At the high-affinity quasi 3-fold sites density with C3 symmetry was present. At the center of each site a pillar of density was evident projecting away from the capsid suggesting that the C-terminus of the Dec protein fused to hCD40L was projected away from the capsid (FIG. 11C). The volume of the additional density at each of the quasi 3-fold sites is ~80-90 nm³. A DechCD40L trimer (105 kDa) would be expected to occupy a volume of 127 nm³ assuming an average density of 1.37 g/cm³. However this experimentally determined volume was still much larger than expected for Dec by itself (57 nm3). This intermediate volume as well as the shape of the density, a pillar that mushrooms as it projects away from the capsid, suggested that hCD40L was directed away from the capsid and remained flexible in the presented context. This flexibility was likely provided, at least in part, by the 8 amino acid glycine-serine linker that separated the Dec domain from the hCD40L domain.

EXAMPLE 9

This example demonstrates the effect of fusion protein saturation of the VLP capsid.

Complete decoration of the P22 capsid for all applications may not be beneficial. More appealing would be a system wherein the degree of polyvalancy, including the number and spacing of presented molecules, could be controlled. If Dec binds in a highly cooperative fashion such that fully decorated capsids are significantly preferred to partially decorated capsids then it may be difficult to control the polyvalency of the Dec-P22 system by simply controlling the stoichiometry of the binding mixture. However previous examination of this system suggests that binding of Dec to the capsid is kinetically fast (kon~10,000 M-1 s-1) and strong ($K_D$~300 pM) suggesting that any cooperativity would be dominated by the already fast kinetics of binding.

To quantify the effects of polyvalent display of hCD40L on the P22 VLP, signaling was monitored in cell culture using a HEK-Blue™ CD40L (InVivoGen) assay. Frozen cells were thawed at 37° C. and immediately transferred to 15 mL of pre-warmed growth media (DMEM, 4.5 g/L glucose, 10% (v/v) fetal bovine serum, 50 U/mL penicillin, 50 mg/mL streptomycin, 2 mM L-glutamine). Cells were centrifuged, resuspended in 1 mL of growth media and transferred to 10 mL of growth media in a T-75 flask. Cells were passaged five times with selective antibiotics (30 µg/ml of Blasticidin and 100 µg/ml of Zeocin) being added after the second passage. Cells were harvested and diluted in growth media to a final concentration of 300,000 cells per mL.

Serial half-log dilutions of DechCD40L and recombinant soluble human CD40L were prepared ranging from 967-0.0097 nM. Variable polyvalency sample sets were created using a constant concentration of DechCD40L (3 nM monomer). The concentration of EX P22 capsid was varied from 10 nM to 0.3 pM such that the stoichiometry of DechCD40L trimers to capsids ranged from 0.1-3162. Control sets were created using the dilutions of EX P22 mixed with recombinant human CD40L at 3 nM, to examine any effects of the CD40L and capsid as an admixture, and using only the EX P22 dilutions to examine the effects of increasing concentrations of P22 alone.

All samples were aliquotted, 20 uL each, into a sterile 96 well plate. To each well 180 µL of cell suspension was added. Plates were incubated for 20 hrs at 37° C., 5% $CO_2$. Media was aliquotted (40 µL) from each sample into a fresh plate. QUANTI-Blue™ reagent suspension was added (160 µL) to each well and plates were incubated at 37° C. The absorbance at 635 nm was measured at 30 and 50 mins after reagent addition. All plates were run in triplicate and all signals were zeroed to a cell-only control well then normalized to the response for 967 nM DechCD40L, which was consistently the most intense signal.

Figure 12A:
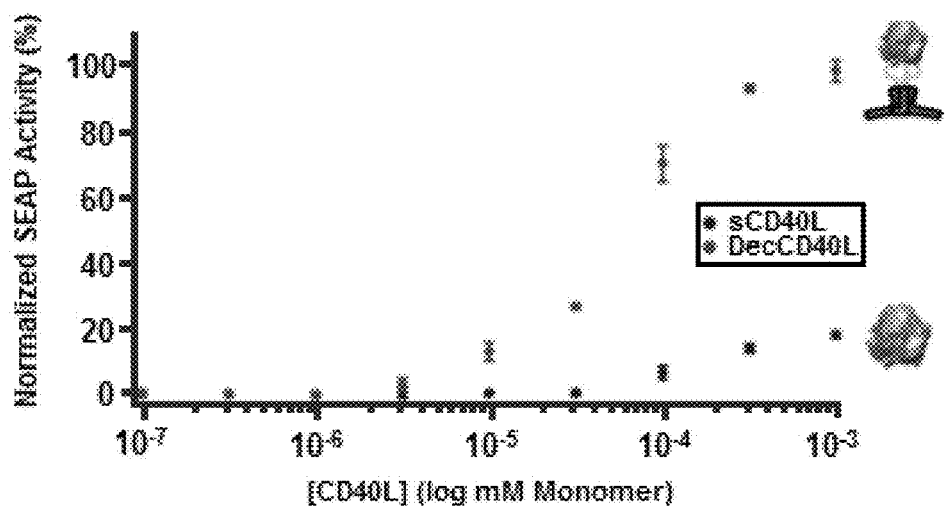
FIGS. 12A-12C demonstrate that DechCD40L exhibits controllable signaling amplification with polyvalent display.

To assess the signaling potential of DechCD40L as a soluble trimer, a concentration series of DechCD40L ranging from 0.1-1000 nM was incubated with cells for 24 hours and the extracellular activity of SEAP were measured. The assay displayed a concentration dependent response to the DechCD40L with near linear sensitivity from 1-100 nM. Surprisingly when this response was compared to soluble hCD40L (shCD40L) trimers at the same concentrations the DechCD40L displayed a much greater signal to concentration response and maximum potential signal (FIG. 12A). The concentration range at which the assay was sensitive was nearly identical between the shCD40L and the DechCD40L. The causes of such an effect remained unclear but potential explanations include Dec-mediated enforcement of the CD40L quaternary structure or transient dimer of trimer formation through self-association of the Dec.

Figure 12B:
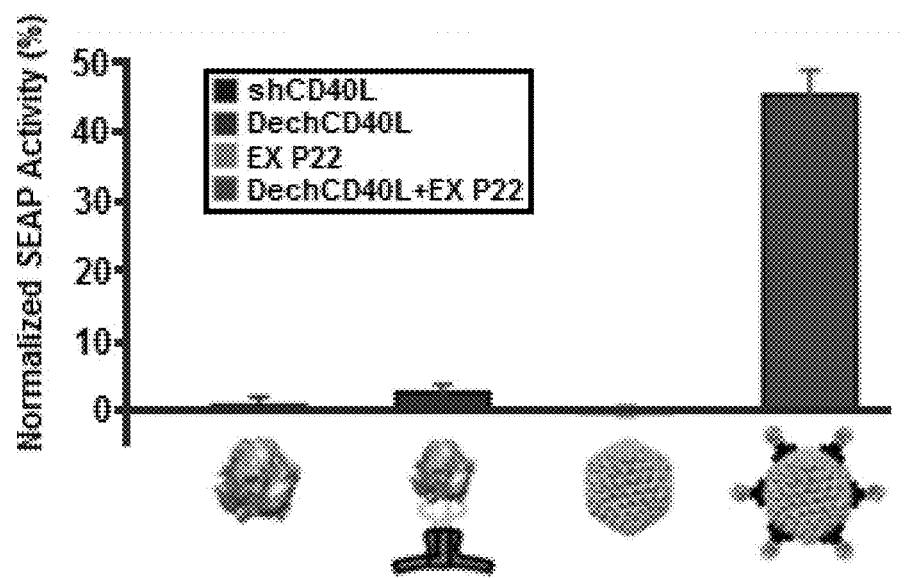

To elucidate the effects polyvalent display, the SEAP response to 3 nM DechCD40L stimulation was compared with and without one equivalent of EX P22. Polyvalent display on EX P22 led to a ~15-fold increase in signaling response compared to DechCD40L alone and a ~50-fold increase compared to free shCD40L. P22 alone was unable to stimulate any SEAP response and a P22+shCD40L admixture generated a response comparable to shCD40L alone (FIG. 12B).

The sizeable net enhancement of signaling from polyvalent display was promising and demonstrated the value of the P22-Dec system for improving potency of CD40L. However a system that can be easily tuned to control the amount of enhancement surpasses the usefulness of a system that is either fully polyvalent or monovalent. The P22-Dec system offers the potential to tune the degree of polyvalency by controlling the stoichiometry of Dec and P22.

Figure 12C:
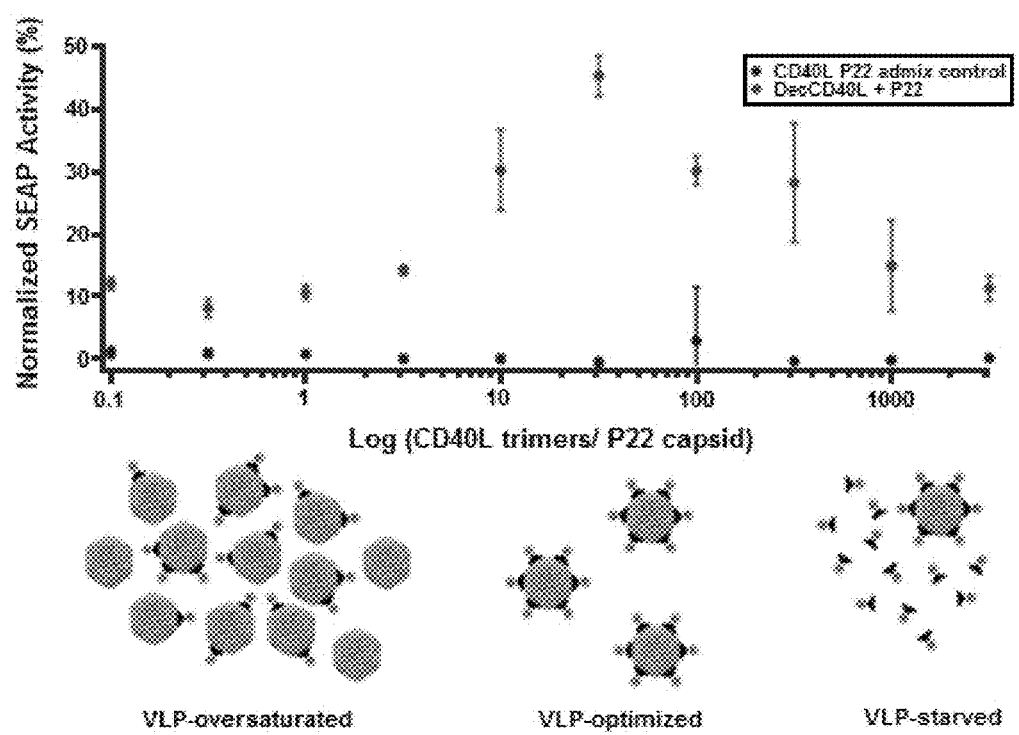

To test the possibility that partially decorated capsids could generate intermediate levels of polyvalent amplification of DechCD40L signaling, a series of different EX P22 to DechCD40L ratios were tested with the absolute concentration of DechCD40L held constant at 3 nM in all samples. By changing the concentration EX P22 the available DechCD40L trimers per capsid was varied from 0.1 in a VLP oversaturated state to 3,000 in a VLP starved state. As expected the ratio of DechCD40L to P22 determined the level of signaling amplification due to polyvalency. The maximum signaling enhancement was centered near the fully decorated capsid ~30-60 trimers per capsid (FIG. 12C). The signal amplification decreased with the ratio of DechCD40L to P22 below full-occupancy to a ratio of ~3 trimers/VLP. Below this ratio activation was insensitive to the ratio trimers/VLP though this was expected because a capsid cannot physically display less than a single trimer. Above the ratio of full occupancy the amplification of signaling also decreased. At these ratios the system was starved of VLP such that every P22 is fully decorated but all extra DechCD40L was in a free monovalent form so the amplification tapers with the concentration of capsid.

These results show that not only can the VLP-Dec display system drastically amplify the signaling of antigen binding domain (e.g., hCD40L) but that the amplification can be tuned via intermediate decoration of the capsid.

Together these results show that the VLP-Dec system can effectively amplify and tune the activity of hCD40L and demonstrates the potential for presentation of other TNFSF members.

EXAMPLE 10

This example demonstrates the creation of a fusion protein comprising a Dec protein and an antigen binding domain.

To examine the potential for Dec to present other members of the TNFSF family a soluble truncated form of TRAIL was fused to the C-terminus of the Dec protein forming a DechTRAIL-T construct. Specifically, an N-terminal 6× histidine tag DecWT gene was ligated into a pET Duet vector via BamHI and SacI sites. A gene fragment coding for a truncated form of human TRAIL (TRAIL-T) and 25 base pair flanking regions matching the target plasmid insertion site was ordered as a gBlock® from Integrated DNA Technologies Inc. DecWT pETDuet was amplified using the Dec_pETDuet fwd and rev primers, which removed the stop codon of the Dec gene.

```
Dec_pETDuet fwd:
                                    (SEQ ID NO: 31)
GAGCTCGGCGCGCCTGCAGGTCGACAAGCTT Dec_pETDuet rev:
                                    (SEQ ID NO: 32)
GGATCCACTTCCTGATGTTGTTTCGATAGTC
```

The DechTRAIL-T plasmid was assembled using NEBuilder® HiFi DNA Assembly Mix as per manufacturer's suggestions. Insertions and mutations were confirmed by DNA sequencing (Eurofins MWG Operon, Inc.).

All constructs were transformed into ClearColi®. Strains harboring expression vectors for TRAIL-T or for the P22 CP and SP were grown on LB medium at 37° C. in the presence of ampicillin to maintain selection for the plasmid. Expression of the genes was induced by addition of isopropyl β-D-thiogalactopyranoside (IPTG) to a final concentration of 0.5 mM once the cells reached mid-log phase (OD600=0.8). Cultures of DechTRAIL-T were briefly cooled on ice at the point of induction and allowed to continue growing at room temperature. Cultures were grown for 4 hours after addition of IPTG, harvested via centrifugation and cell pellets stored at −20° C. overnight.

Cell pellets were resuspended in PBS (50 mM sodium phosphate, 100 mM sodium chloride, pH 7.0) with lysozyme, DNAse and RNAse added and incubated at room temperature for 30 minutes. The cell suspension was lysed by sonication. Cellular components were removed by centrifugation at 12,000 g for 45 min at 4° C. P22: P22 samples were purified from the post-lysis supernatant by ultracentrifugation through a 5 mL 35% (w/v) sucrose cushion. The resulting viral pellet was resuspended in PBS (50 mM sodium phosphate, 100 mM sodium chloride, pH 7.0) and centrifuged at 16,000 g for 20 min to remove any remaining aggregates. Samples were then purified over an S-500 Sephadex (GE Healthcare Life Sciences) size exclusion column using a Biorad Biologic Duoflow FLPC. Fractions containing P22 were concentrated by ultracentrifugation and the resulting viral pellet was resuspended in an adequate volume of PBS or HBS (50 mM HEPES, 100 mM NaCl, pH 7.0). Dec: All his-tagged constructs were purified using a 5 mL Rosche cOmplete his-tag purification column. Samples were loaded onto the column in PBS at 2 mL/minute and washed with 40 mL of 50 mM phosphate, 100 mM sodium chloride, 20 mM imidazole pH 7.5. Samples were eluted with an 80 mL gradient from 20-125 mM imidazole. Fractions were collected based on $A_{280}$ and the pooled fractions were dialyzed into PBS or HBS overnight. Samples were concentrated by rebinding to His-tag column, washing with 40 mL of 20 mM imidazole and stepwise elution with 250 mM imidazole in either PBS or HBS. Samples were dialyzed as before to remove imidazole. Concentrations of each construct were determined by UV absorption measured at 280 nm under denatured conditions (5M guanidine hydrochloride) using extinction coefficients calculated using Protein Calculator v3.3 (Chris Putnam, Scripps).

Procapsid P22 at 2 mg/mL was heated for 25 min in a water bath at 67° C. Expansion was confirmed via non-denaturing 1% agarose gel electrophoresis at 65 volts for 2 hours in TAE buffer (40 mM Tris, 20 mM acetate, 1 mM EDTA pH 8.0) stained with InstantBlue™.

Figure 13A:
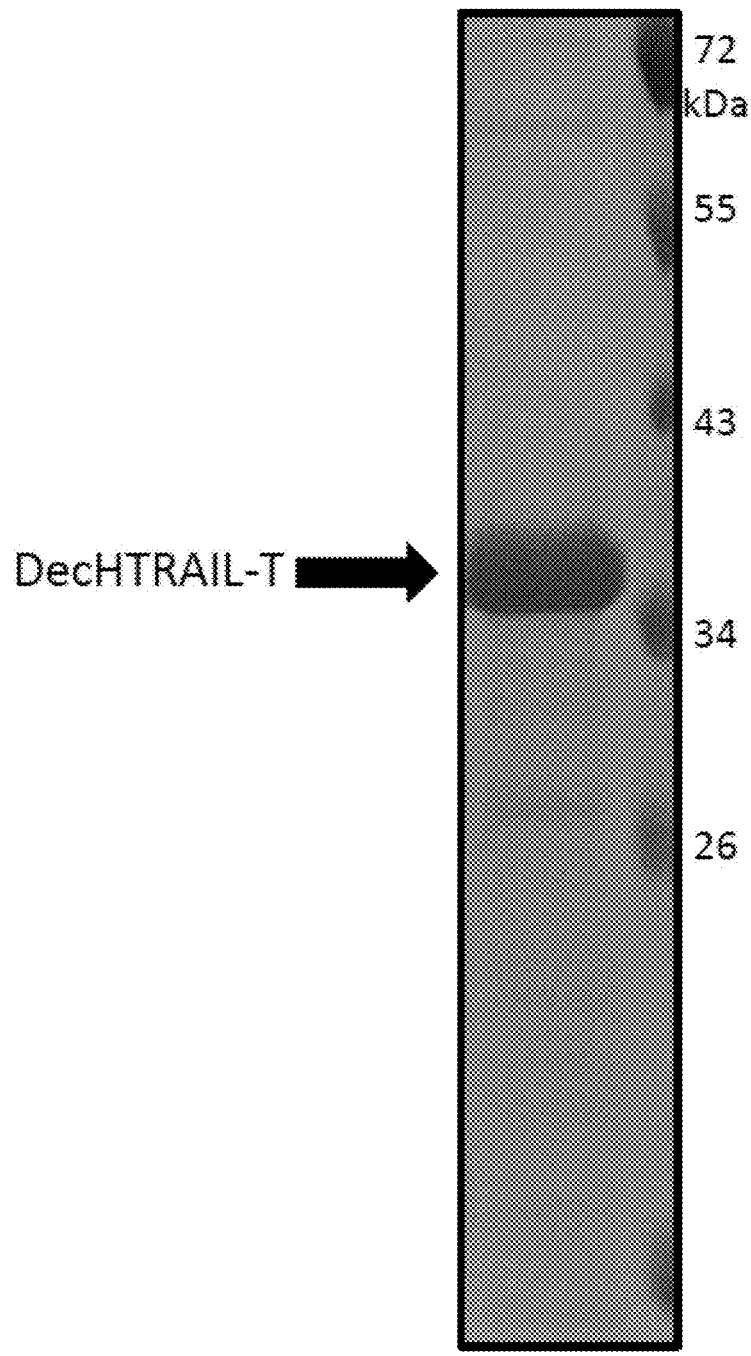
FIGS. 13A-13B depict results of experiments demonstrating that the inventive fusion protein is readily expressed and purified.
Figure 13B:
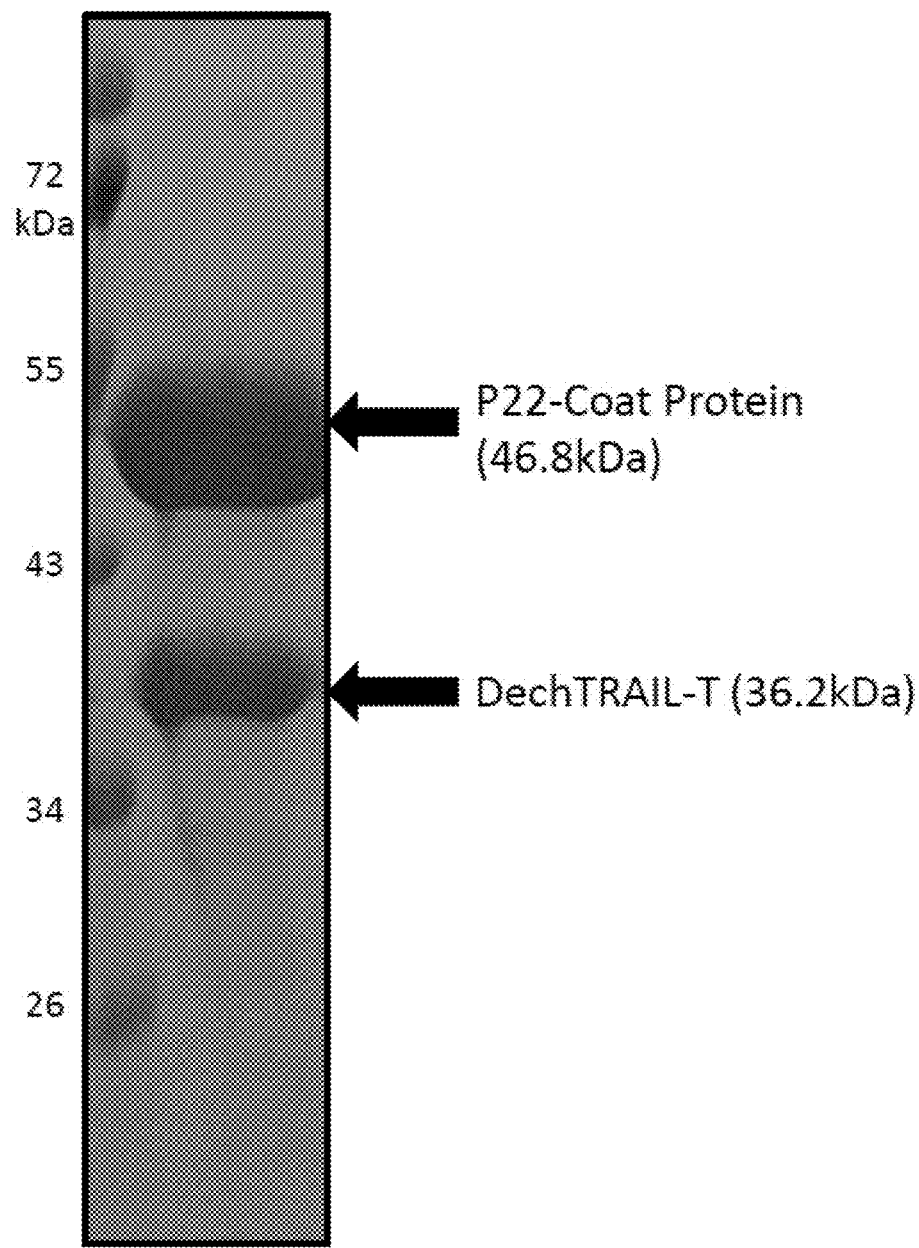

Expression of DechTRAIL-T and purification via an N-terminal 6× histidine tag resulted in a band by SDS-Page, which matched well with the expected molecular weight of 36.2 kDa (FIG. 13A). Initial mixture with EX P22 followed by ultracentrifugation demonstrated that DechTRAIL-T binds to the capsid and the identity was further confirmed by western blot analysis using a polyclonal anti-Dec Ab mixture (FIG. 13B).

EXAMPLE 11

This example demonstrates the anti-cancer efficacy of the fusion protein comprising a Dec protein and an antigen binding domain To determine if the DechTRAIL-T construct was able to induce cellular apoptosis, HeLa cells were incubated with indicated amount of DechTRAIL-T (TRAIL), Dech-TRAIL-T (TRAIL) bound to P22, or P22 alone. Apoptosis was monitored using Resazurin dye, which is a colormetric dye used to monitor live vs dead cells. Reduction is metabolism of Resazurin indicates cell death. Controls used were Resazurin dye in culture media with no cells to give a background reading, cells with only dye added (negative control) and cells incubated with Zinc Chloride to induce cell death (positive control).

Figure 14:
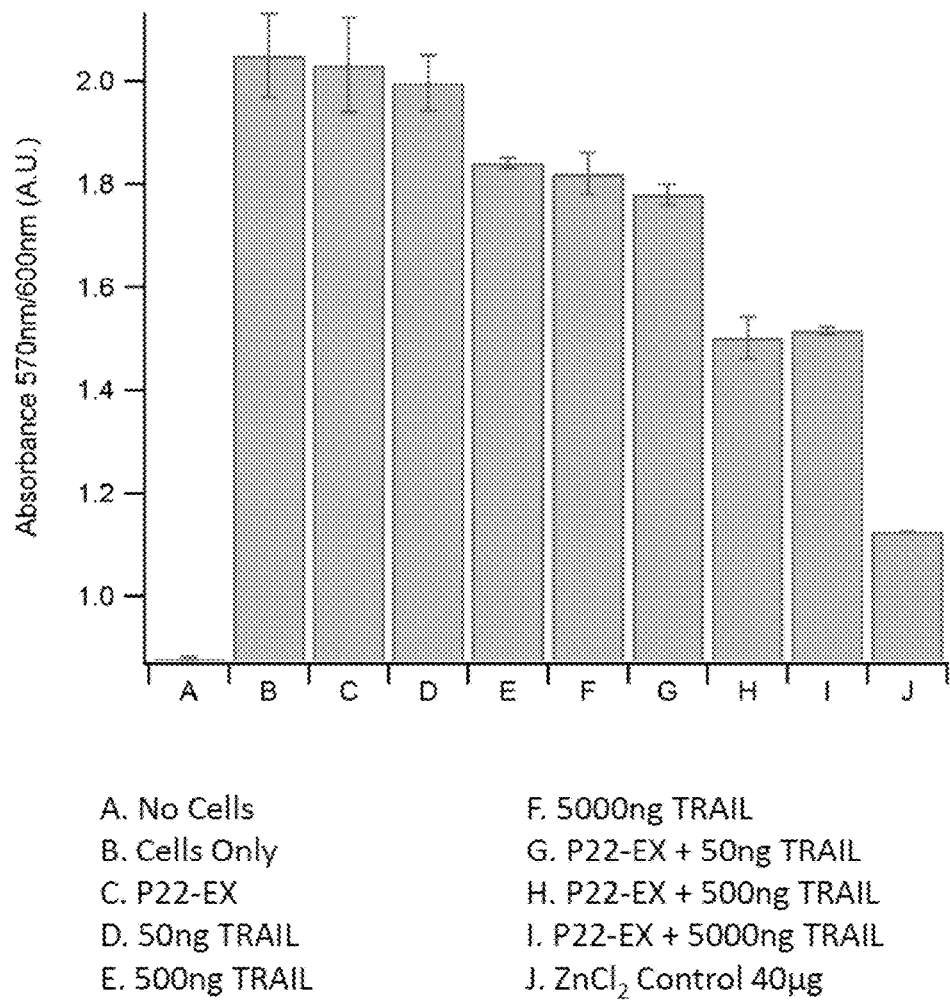
FIG. 14 is a graph illustrating the results of experiments demonstrating the anticancer efficacy of the inventive fusion protein. Briefly, cells incubated with the indicated amount of free DechTRAIL-T showed dose-dependent induction of apoptosis, which increased when DechTRAIL-T was bound to P22 before incubation. Controls used were Resazurin dye in culture media with no cells to give a background reading, cells with only dye added (negative control) and cells incubated with Zinc Chloride to induce cell death (positive control).

The result of this study shows that treatment with DecH-TRAIL-T alone lead to a dose-dependent induction of apoptosis in the HeLa cells. Further, the amount of apoptosis increased when DechTRAIL-T was bound to P22 prior incubation (FIG. 14).

These results demonstrate that the inventive fusion proteins alone or bound to the VLP have a robust anticancer effect.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A fusion protein comprising an antigen binding domain of a trimerizable tumor necrosis factor super family (TNFSF) protein, and the fusion protein further comprising a trimerizable double stranded DNA bacteriophage decoration (Dec) accessory coat protein.

2. The fusion protein of claim 1, wherein the antigen binding domain and the Dec protein are joined via a linker region.

3. The fusion protein of claim 2, IA/herein the linker region comprises 1-100 amino acids.

4. The fusion protein of claim 3, wherein the linker region comprises glycine and serine residues.

5. The fusion protein of claim 1, further comprising a tag.

6. The fusion protein of claim 5, wherein the tag is a polyhistidine tag.

7. The fusion protein of claim 1, wherein the C-terminus of the Dec protein is linked to the N-terminus of the antigen binding domain.

8. The fusion protein of claim 1, wherein the Dec protein is a bacteriophage L Dec protein.

9. A polynucleotide encoding the fusion protein of claim 1.

10. A recombinant vector comprising the polynucleotide of claim 9.

11. The vector of claim 10, further comprising a promoter region operably linked to the polynucleotide.

12. A composition comprising the fusion protein of claim 1 and a virus like particle (VLP).

13. The composition of claim 12, wherein the VLP is a bacteriophage VLP.

14. The composition of claim 13, wherein the bacteriophage VLP is a bacteriophage P22, VLP.

15. The composition of claim 12, wherein the VLP encapsulates a guest protein.

16. The, fusion protein of claim 1, wherein the TNSF protein is a mammalian TNSF protein.

17. The fusion protein of claim 16, wherein the double stranded DNA bacteriophage decoration (Dec) accessory coat protein can bind to a virus like particle (VLP).

18. A fusion protein comprising an antigen binding domain of a trimerizable tumor necrosis factor super family (TNFSF) protein, the fusion protein further comprising a trimerizable double stranded DNA bacteriophage decoration (Dec) accessory coat protein, and wherein the TNFSF protein is selected from the group consisting of: TNF-α, VEGI, 4-1BBL (TNFSF9), CD 27L (CD70), GIRTL, TRAIL, APRIL, BAFF, FASL, EDA, TWEAK, Lymphotoxin beta, Lymphotoxin alpha, LIGHT, CD30L, RANKL, OX40L, and CD40L.

19. The fusion protein of claim 18, wherein the TNFSF protein is selected from the group consisting of: CD40L, TRAIL, CD70, 1BBL, MITRE, and TRAIL-T.

20. A fusion protein comprising an antigen binding domain of a trimerizable tumor necrosis factor super family (TNFSF) protein, and the fusion protein further comprising a trimerizable double stranded DNA bacteriophage decoration (Dec) accessory coat protein, wherein the TNFSF protein is CD40L.

21. The fusion protein of claim 20, wherein the CD40L is murine CD40L, (mCD40L) or human CD40L, (hCD40L).

* * * * *